US009847012B2

(12) United States Patent
Zomet et al.

(10) Patent No.: US 9,847,012 B2
(45) Date of Patent: Dec. 19, 2017

(54) MEAL-BASED MEDICATION REMINDER SYSTEM

(71) Applicant: Google Inc., Mountain View, CA (US)

(72) Inventors: Asaf Zomet, Jerusalem (IL); Michael Shynar, Tel-Aviv (IL)

(73) Assignee: Google LLC, Mountain View, CA (US)

( * ) Notice: Subject to any disclaimer, the term of this patent is extended or adjusted under 35 U.S.C. 154(b) by 27 days.

(21) Appl. No.: 14/324,769

(22) Filed: Jul. 7, 2014

(65) Prior Publication Data

US 2016/0005299 A1  Jan. 7, 2016

(51) Int. Cl.
 G08B 23/00 (2006.01)
 G08B 21/24 (2006.01)
 G06F 19/00 (2011.01)

(52) U.S. Cl.
 CPC ......... G08B 21/24 (2013.01); G06F 19/3456 (2013.01)

(58) Field of Classification Search
 CPC ............................ G08B 21/24; G06F 19/3456
 See application file for complete search history.

(56) References Cited

U.S. PATENT DOCUMENTS

| 4,836,778 | A | 6/1989 | Baumrind et al. | |
|---|---|---|---|---|
| 6,696,924 | B1* | 2/2004 | Socinski | G06F 19/3456 221/15 |
| 8,040,236 | B2* | 10/2011 | Larsen | G06F 19/3418 340/309.16 |
| 8,742,936 | B2* | 6/2014 | Galley | B60K 28/066 340/439 |
| 9,047,746 | B1* | 6/2015 | Euliano, II | G08B 23/00 |
| 2008/0276461 | A1 | 11/2008 | Gold | |
| 2009/0050645 | A1* | 2/2009 | Burg | G06F 19/3462 221/15 |
| 2010/0305468 | A1* | 12/2010 | Policker | A61N 1/36007 600/547 |
| 2011/0124996 | A1* | 5/2011 | Reinke | A61M 5/14248 600/365 |
| 2011/0153361 | A1* | 6/2011 | Hanina | G06Q 10/10 705/3 |

(Continued)

OTHER PUBLICATIONS

Richardson, "Never forget to take your pills with Medication Reminder for BlackBerry smartphones," CrackBerry, Jun. 18, 2012, Retrieved from the internet <http://crackberry.com/never-forget-take-your-pills-medication-reminder-blackberry-smartphones> 3 pp.

(Continued)

Primary Examiner — Quang D Pham
(74) Attorney, Agent, or Firm — Shumaker & Seiffert, P.A.

(57) ABSTRACT

In general, this disclosure is directed to techniques for generating, by a computing device, at approximately a time that a user is eating, at least one computer-generated indication. Based at least in part on the at least one computer-generated indication and pre-defined activity data that are indicative of a human consuming an ingestible substance, the computing device determines whether the user is currently consuming an ingestible substance. Responsive to determining that the user is currently consuming the ingestible substance, the computing device outputs a reminder to consume at least one particular ingestible substance, such as a medication.

17 Claims, 8 Drawing Sheets

(56) References Cited

U.S. PATENT DOCUMENTS

| | | | | |
|---|---|---|---|---|
| 2011/0270052 | A1* | 11/2011 | Jensen | A61B 5/0002 600/302 |
| 2011/0276312 | A1* | 11/2011 | Shalon | A61B 5/11 702/187 |
| 2012/0022443 | A1* | 1/2012 | Robertson | A61M 5/1723 604/65 |
| 2012/0179012 | A1* | 7/2012 | Saffarian | A61B 5/0022 600/324 |
| 2013/0035871 | A1* | 2/2013 | Mayou | A61B 5/14532 702/26 |
| 2013/0138230 | A1* | 5/2013 | Landers | G06F 17/40 700/91 |
| 2013/0217982 | A1* | 8/2013 | Behzadi | A61B 5/0022 600/302 |
| 2013/0267794 | A1 | 10/2013 | Fernstrom et al. | |
| 2013/0336519 | A1 | 12/2013 | Connor | |
| 2013/0338628 | A1* | 12/2013 | Robertson | A61M 5/1723 604/503 |
| 2014/0129253 | A1* | 5/2014 | Hanina | G06Q 10/10 705/2 |
| 2014/0203950 | A1* | 7/2014 | Zdeblick | G06F 19/3418 340/870.07 |
| 2014/0276244 | A1* | 9/2014 | Kamyar | A61B 5/1112 600/595 |
| 2014/0377724 | A1* | 12/2014 | Hoover | G09B 19/0092 434/127 |
| 2015/0168365 | A1* | 6/2015 | Connor | G01N 33/02 356/51 |
| 2015/0238139 | A1* | 8/2015 | Raskin | A61B 5/4866 600/595 |
| 2016/0026767 | A1* | 1/2016 | Sarrafzadeh | G06Q 50/22 600/586 |
| 2016/0192039 | A1* | 6/2016 | Negi | H04Q 9/00 340/870.07 |

OTHER PUBLICATIONS

International Search Report and Written Opinion of International Application No. PCT/US2015/039052, dated Oct. 2, 2015, 13 pp.

Kaushik et al., "Observations From a Case Study on User Adaptive Reminders for Medication Adherence," Second International Conference on Pervasive Computing Technologies for Healthcare, Pervasive Health 2008, Jan. 30-Feb. 1, 2008, 4 pp.

Liu et al., "An Intelligent Food-Intake Monitoring System Using Wearable Sensors," 2012 Ninth International Conference on Wearable and Implantable Body Sensor Networks, IEEE, May 9, 2012, 7 pp.

Pentland, "Healthwear: Medical technology becomes wearable," Computer Society, vol. 37, No. 5, May 2004, 8 pp.

Zhang et al., "Detection of activities for daily life surveillance: Eating and drinking," 2008 10th International Conference on e-Health Networking, IEEE, Jul. 7, 2008, 6 pp.

International Preliminary Report on Patentability from International Application No. PCT/US2015/039052, dated Jan. 19, 2017, 9 pp.

* cited by examiner

MEAL-BASED MEDICATION REMINDER SYSTEM

BACKGROUND

A person may take medications on a schedule to improve efficacy of the medications and/or to reduce attendant side effects. Reminders that are output by a computing device may assist a person to stay on a necessary schedule for the regular ingestion or application of a variety of medications. While some schedules for medication are strictly time based, others are more temporally flexible and may only require dosages within some range of time. For instance, some medications may be taken by a person within a range of time before, during, or after the consumption of food, such as a meal. However, given the variability of individuals' eating patterns, time-based medication reminders which only account for the time at which a medication must be taken may not correspond to when an individual is actually eating or about to eat.

SUMMARY

In one example, a method includes generating, by a computing device at approximately a time that a user is eating, at least one computer-generated indication; determining, by the computing device and based at least in part on the at least one computer-generated indication and pre-defined activity data that are indicative of an act of a human consuming an ingestible substance, whether the user is currently consuming an ingestible substance; and responsive to determining that the user is currently consuming an ingestible substance, outputting, by the computing device, a reminder to consume at least one particular ingestible substance.

In another example, a computing device includes at least one processor and at least one module, operable by the at least one processor to generate, at approximately a time that a user is eating, at least one computer-generated indication, determine, based at least in part on the at least one computer-generated indication and pre-defined activity data that are indicative of an act of a human consuming an ingestible substance, whether the user is currently consuming an ingestible substance, and, responsive to determining that the user is currently consuming an ingestible substance, output a reminder to consume at least one particular ingestible substance.

In another example, a computer-readable storage medium is encoded with instructions that, when executed, cause at least one processor of a computing device to generate, at approximately a time that a user is eating, at least one computer-generated indication; determine, based at least in part on the at least one computer-generated indication and pre-defined activity data that are indicative of an act of a human consuming an ingestible substance, whether the user is currently consuming an ingestible substance; and responsive to determining that the user is currently consuming an ingestible substance, output a reminder to consume at least one particular ingestible substance.

The details of one or more examples of the disclosure are set forth in the accompanying drawings and the description below. Other features, objects, and advantages will be apparent from the description and drawings, and from the claims.

DETAILED DESCRIPTION

In general, techniques of this disclosure are directed to outputting a reminder indicating that a user should take a medication based on a determination that the user is currently eating. A computing device may compare relevant sensor and/or other data to predetermined values to determine whether the user is eating, rather than making the determination based solely on time or location. Examples of such data include pictures of food in front of the user, a picture of utensils, motion data obtained from one or more sensors of or operatively coupled to the computing device, a blood sugar level of the user as measured by the computing device or a device operatively coupled thereto, a sound detected by the computing device or a device operatively coupled thereto, a picture of a cheekbone of the user, etc.

To illustrate, as the user is eating, one or more sensors and/or input devices of or operatively coupled to the computing device may generate data for a user in determining whether the user is currently eating. The computing device may classify the generated data, based on pre-defined activity data that are indicative of an act of a human eating, to determine whether the user is actually eating at the current time. In this manner, techniques of the disclosure may provide more accurate medication reminders, thereby reducing the number of instances that a user must manually check a computing device to determine whether to ingest medication.

Figure 1:
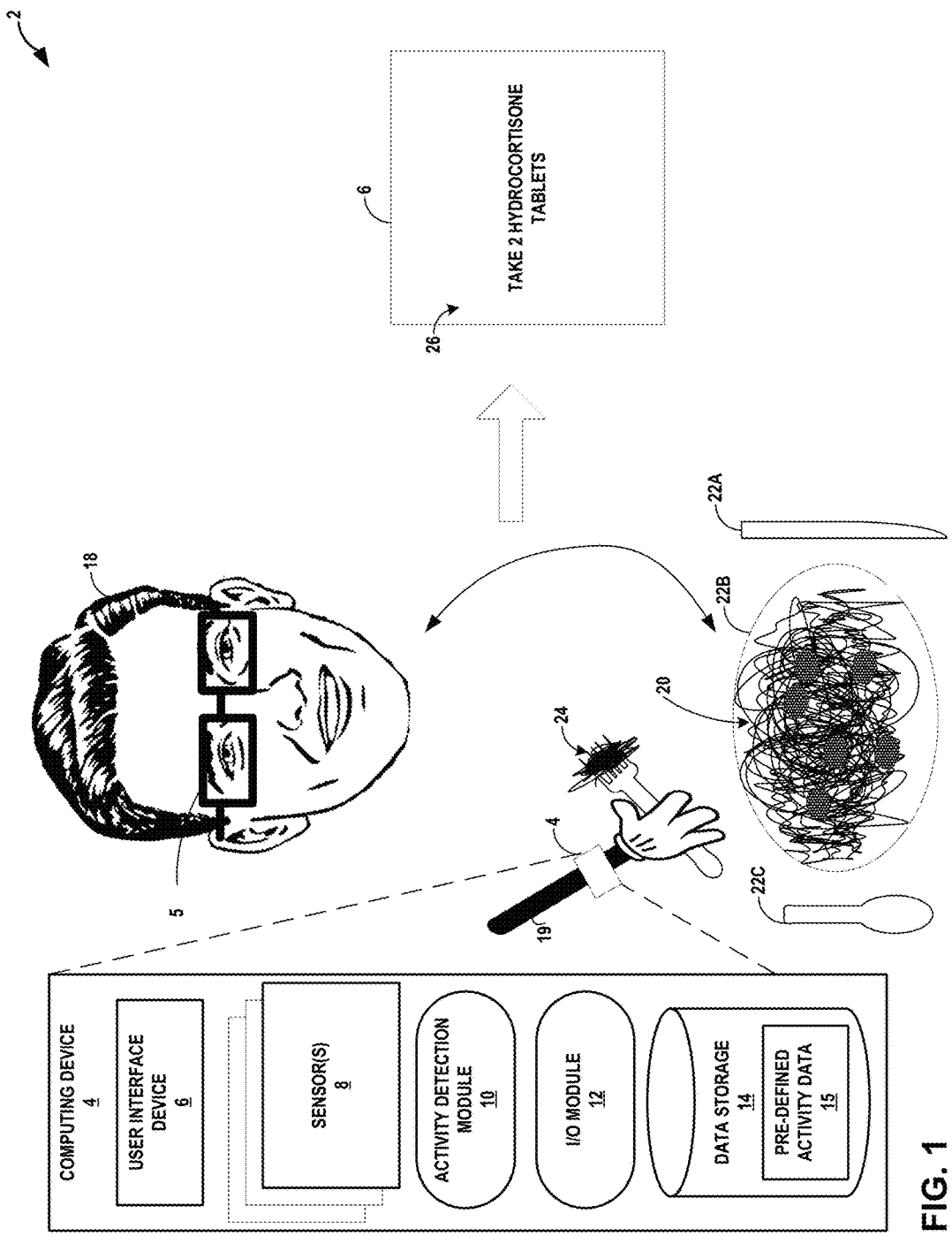
FIG. 1 is a conceptual diagram illustrating an example system including a computing device that determines whether a user is consuming an ingestible substance and outputs a reminder to consume at least one particular ingestible substance, in accordance with one or more aspects of the present disclosure.

FIG. 1 is a conceptual diagram illustrating an example system including a computing device that determines whether a user is consuming an ingestible substance and outputs a reminder to consume at least one particular ingestible substance, in accordance with one or more aspects of the present disclosure. As further described below, based on the at least one computer-generated indication and pre-defined activity data, a computing device may determine that a user is eating and output a reminder to take a medication. As shown in FIG. 1, system 2 includes computing device 4 and, in some examples, computing device 5.

In the example of FIG. 1, computing device 4 is a wearable computing device, such as a smartwatch. However, in some examples, computing device 4 may be a computerized watch, computerized eyewear, computerized headwear, computerized gloves, a blood sugar monitoring device (e.g., a sugar-measuring lens), a tablet computer, a mobile phone, a personal digital assistant (PDA), a laptop computer, a gaming system, a media player, an e-book reader, a television platform, an automobile navigation system, a camera, one or more sensors, or any other type of mobile and/or non-mobile computing device that is configured to measure one or more characteristics of a user, such as motion, environment, or bodily state and generate an indication of the one or more characteristics.

Computing device 4 further includes user interface device (UID) 6, one or more sensors 8, activity detection module 10, input/output (I/O) module 12, and data storage 14. Modules 10 and 12 may perform operations described herein using software, hardware, firmware, or a mixture of hardware, software, and/or firmware residing in and/or executing at computing device 4. Computing device 4 may execute modules 10 and 12 with one or more processors. In some examples, computing device 4 may execute modules 10 and 12 as one or more virtual machines executing on underlying hardware of computing device 4. Modules 10 and 12 may execute as one or more services or components of operating systems or computing platforms of computing device 4. Modules 10 and 12 may execute as one or more executable programs at application layers of computing platforms of computing device 4. In some examples, UID 6, one or more sensors 8, data storage 14 and/or modules 10 and 12 may be arranged remotely to and be remotely accessible to computing device 4, for instance, via interaction by computing device 4 with one or more network services operating in a network cloud.

In some examples, multiple computing devices may be used. For instance, computing device 5, which may be any of the computing devices listed as examples above for computing device 4, is illustrated as computerized eyewear. Computing device 5 may be used in conjunction with computing device 4 to determine multiple characteristics and/or actions of a user and characteristics of an environment of the user to create at least one computer-generated indication that is indicative of consuming an ingestible substance.

UID 6 of computing device 4 may include respective input and/or output devices for computing device 4. UID 6 may be implemented using one or more various technologies. For instance, UID 6 may function as input device using a presence-sensitive input screen, such as a resistive touchscreen, a surface acoustic wave touchscreen, a capacitive touchscreen, a projective capacitance touchscreen, a pressure sensitive screen, an acoustic pulse recognition touchscreen, or another presence-sensitive display technology. UID 6 may function as output (e.g., display) device using any one or more display devices, such as a liquid crystal display (LCD), a dot matrix display, a light emitting diode (LED) display, an organic light-emitting diode (OLED) display, e-ink, or similar monochrome or color displays capable of outputting visible information to a user of computing device 4.

In some examples, UID 6 may include a presence-sensitive display that may include a display device and receive tactile input from a user of computing device 4. UID 6 may receive indications of tactile input by detecting one or more gestures from a user (e.g., the user touching or pointing to one or more locations of UID 6 with a finger or a stylus pen). UID 6 may present output to a user, for instance at a presence-sensitive display. UID 6 may present the output as a graphical user interface (e.g., a user interface for viewing an alert based on notification data), which may be associated with functionality provided by computing device 4. For example, UID 6 may present various user interfaces related to the functionality of computing platforms, operating systems, applications, and/or services executing at or accessible by computing device 4 (e.g., notification services, electronic message applications, Internet browser applications, mobile or desktop operating systems, etc.). A user may interact with a user interface presented at UID 6 to cause computing device 4 to perform operations relating to functions.

I/O module 12 may receive and interpret inputs detected at UID 6 (e.g., as a user provides one or more gestures at one or more locations of UID 6 at which a user interface is displayed) and input detected at other input devices of computing device 4 (e.g., microphones, cameras, sensors, physical buttons, etc.). I/O module 12 may relay information about the input detected at computing device 4 to one or more associated platforms, operating systems, applications, and/or services executing at computing device 4, to cause computing device 4 to perform functions.

I/O module 12 also may receive information and instructions from one or more associated platforms, operating systems, applications, and/or services executing at computing device 4 (e.g., activity detection module 10, etc.) for generating a graphical user interface or for providing a somatosensory type user interface. In addition, I/O module 12 may act as a respective intermediary between the one or more associated platforms, operating systems, applications, and/or services executing at computing device 4 and various output devices of computing device 4 (e.g., UID 6, one or more sensors 8, data storage 14, a speaker, a LED indicator, other output devices, etc.) to produce output (e.g., a graphic, a flash of light, a sound, a somatosensory response, a haptic response, etc.) with computing device 4.

As shown in FIG. 1, computing device 4 may include one or more sensors 8 (sensors 8). Sensors 8 may include an accelerometer that generates accelerometer data. Accelerometer data may indicate an acceleration and/or a change in acceleration of computing device 4. Sensors 8 may include a gyrometer that generates gyrometer data. Gyrometer data may indicate a physical orientation and/or change in physical orientation of computing device 4. In some examples, the orientation may be relative to one or more reference points. Sensors 8 may include a magnetometer that generates magnetometer data. Magnetometer data may indicate the magnetization of an object that is touching or in proximity to computing device 4. Magnetometer data may indicate the Earth's magnetic field, and in some examples, provide directional functionality of a compass.

Sensors 8 may include an ambient light sensor that generates ambient light data. The ambient light data may indicate an intensity of light to which computing device 4 is exposed. Sensors 8 may include a proximity sensor that generates proximity data. Proximity data may indicate whether an object is within proximity to computing device 4. In some examples, proximity data may indicate how close an object is to computing device 4. In some examples, sensors 8 may include a clock that generates a date and time. The date and time may be a current date and time. Sensors 8 may include a pressure sensor that generates pressure data. Pressure data may indicate whether a force is applied to computing device 4 and/or a magnitude of a force applied to computing device 4. Pressure data may indicate whether a force is applied to UID 6 and/or a magnitude of a force applied to UID 6. Sensors 8 may include a video sensor that generates picture or video data. Picture or video data may be used to further sense motions of various body parts of a user or a user's surroundings, such as food or a place setting on a table in front of a user. Sensors 8 may include a global positioning system that generates location data. Sensors 8 may also include a clock that generates time data. As shown in FIG. 1, computing device 4 may include one or more data storage devices 14 ("data storage 14") within computing device 4 may store information for processing during operation of computing device 4.

Data storage 14 may be configured to hold medical records and prescription information accessible by I/O module 12 in order to ascertain what medications a user should take in response to activity detection module 10 determining that the user is currently consuming an ingestible substance. In some examples, data storage 14 may be one or more files, databases, tables, lists, or any other suitable data structures that may store, access and modify data. Data storage 14 may further hold pre-defined activity data 15, such as at least one of image data of portions of food, a motion profile, image data of portions of a cheekbone, image data of portions of utensils, a mapping service to look up a restaurant, an eating schedule, an eating time, ambient audio to determine co-presence of others who are eating, a blood sugar level, motion data, a database of coordinates of restaurants, and weighted difference values.

Pre-defined activity data 15 may be collected as a labeled training set, or sensor measurements and their labeling as to whether a person is eating or not eating, measured from either a single user or multiple users. Pre-defined activity data 15 may also include a trained classifier using a process such as Neural Network or Support Vector Machine. Although data storage 14 and pre-defined activity data 15 are shown as included in computing device 4, in some examples, data store 14 and/or pre-defined activity data 15 may be included on a remote computing device and/or may be distributed on multiple computing devices, such as a remote computing device and computing device 4.

Activity detection module 10 may process data received by computing system 2. For example, activity detection module 10 may generate at least one computer-generated indication based on data obtained by sensors 8 and determine, based at least in part on the at least one computer-generated indication and pre-defined activity data 15 that is indicative of a user consuming an ingestible substance, whether the user is currently consuming an ingestible substance. For example, if computing device 4 is a blood sugar measuring device, sensors 8 may receive data indicating a rise in the user's blood sugar levels. Activity detection module 10 may compare this rise in blood sugar levels to a typical blood sugar level increase for the user and determine, based on the rise in blood sugar, that the user is currently eating. Activity detection module 10 may communicate this indication to I/O module 12, which will access medical records stored in data storage 14 to determine whether to output a reminder to consume medication. The medical records may include but are not limited to, dosage information about medication, timing information that indicates when and/or how frequently to take the medication, interaction precaution information to prevent reminders for drugs that may interact in a manner adverse to the user, to name only a few examples.

To illustrate, in the example of FIG. 1, user 18 may be in front of a plate 22B of spaghetti and meatballs 20 with utensils 22A and 22C next to plate 22B. User 18 may be wearing computing device 4, such as a smartwatch, on user's arm 19. In some examples, user 18 may further be wearing computing device 5 (e.g., computerized eyeglasses) on user's 18 face. User 18 may also have a condition such as arthritis. In order to treat the user's arthritis, user 18 may have a prescription of hydrocortisone, a medication that can cause nausea-type side-effects if taken without food.

While wearing computing device 4, user 18 may begin eating spaghetti and meatballs 20 using fork 24. In this example, sensors 8 of computing device 4 may include an accelerometer and a gyrometer. Sensors 8 may measure the position and speed of arm 19 and send that motion data to I/O module 12, which forwards the motion data to activity detection module 10. In some examples that include computing device 5, sensors in computing device 5 (which may include any one or more of sensors 8 described above) may include a camera and take pictures of the plate of food, the utensils, and/or the user 18's cheekbone. Sensors in computing device 5 may also take video of user 18's jawbone motions. Computing device 5 may send this picture and video data to an I/O module in computing device 5, which may forward the picture and video data to either an activity detection module in computing device 5 or I/O module 12 of computing device 4. Generally, a computer-generated indication may be any data that is indicative of a user consuming an ingestible substance and that is received, sent, generated, and/or otherwise defined by a computing device or a device operatively coupled to the computing device (e.g., input devices, sensors, clocks, radios, to name only a few examples).

Activity detection module 10 may, based on the data received from sensors 8 or I/O module 12, generate, at approximately a time the user is eating, at least one computer-generated indication. In some examples, the computer-generated indication may be the unaltered data received from sensors 8 or I/O module 12. In some examples, the computer-generated indication may be data that is based on processing or otherwise transforming the unaltered data received from sensors 8 and/or I/O module 12. For instance, activity detection module 10 may further process the data received from sensors 8 or I/O module 12. As an example, in the example of FIG. 1, activity detection module 10 may perform calculations on motion data measured by an accelerometer and/or gyrometer to convert that motion data into a vector or a series of vectors. In some examples, activity detection module 10 may alter video data measured by a camera to only include frames where the subject of the video is moving above a certain threshold level of motion. Other types of computer-generated indications may include, (altered or unaltered) a picture of food, a picture of utensils, motion data obtained from one or more sensors, a blood sugar level, a time, a sound, a picture of a cheekbone, and GPS coordinates.

In general, a time duration may comprise a range of time, and generating, at approximately a time that a user is eating, the at least one computer-generated indication at the time that the user is eating is within the time duration. In some examples, approximately at a time the user is eating may include a time duration of 5 minutes. In some examples, approximately at a time the user is eating may include a time duration that of 15 minutes, 30 minutes, or a range of 0-1 hour. In some examples, the time duration is manually set by the user. In some examples, the duration is set by the application developer. In some examples, the duration is based on one or more events, such as the range could be condition on whether the user is in motion, has a reservation on a calendar, or whether the user indicates a particular time at which the user may be eating.

Activity detection module 10 may determine, based on the at least one computer-generated indication and pre-defined activity data that are indicative of an act of a human consuming an ingestible substance, whether the user is currently consuming an ingestible substance. As shown in FIG. 1, computing device 4, using activity detection module 10, may compare the motion data, such as motion vectors from a computing device attached to a wrist of a user that measure the motion the user's wrist takes from going between a plate of food and the user's mouth, received from sensors 8 or I/O module 12 to, such as motion vectors from a computing device attached to a wrist of a user that measure the motion the user's wrist takes from going between a plate of food and the user's mouth, pre-defined activity data 15 in data storage 14. For example, pre-defined activity data 15 may be a set of motion data that is indicative of a person eating, and comparing the pre-defined activity data 15 with the computer-generated indication may provide a set of difference values indicative of how close the user 18's motion of moving fork 24 from plate 20 to the user's mouth was to the pre-defined activity data 15 of a user eating in data storage 14.

In some examples, such as using the picture and video data captured by computing device 5, activity detection module 10 may compare a picture of the food to a set of stored pictures of food to determine if user 18 has a plate of food in front of them. Activity detection module 10 may also compare a picture of utensils 22A-22C taken by computing device 5 to a set of stored pictures of utensils to determine if user 18 has a table setting in front of them, which may be indicative that user 18 is eating or about to eat. Further, activity detection module 10 may compare pictures of user 18's cheekbone to a set of stored pictures of cheekbones, wherein the stored pictures of cheekbones are pictures taken when a user is in the act of eating. In still other examples, activity detection module 10 may compare the video data of user 18's jawbone moving to pre-recorded videos of moving jawbones taken while a person was eating to determine if user 18's jawbone is moving how a jawbone would typically move during the act of eating.

Other examples of pre-defined activity data include image data of portions of food, a motion profile, image data of portions of a cheekbone, image data of portions of utensils, a mapping service to look up a restaurant, an eating schedule, an eating time, ambient audio to determine co-presence of others who are eating, a blood sugar level, motion data, a database of coordinates of restaurants, and a trained classifier.

In some examples, such as the example where the pre-defined activity data 15 comprises at least a trained classifier, comparisons may not be made. Instead, computing device 4 may train a classifier using a process such as Neural Network or Support Vector Machine (SVM). Computing device 4 may train the classifier based on any of the other afore-mentioned pre-defined activity data alone or in combination, such as image data of portions of food, a motion profile, image data of portions of a cheekbone, image data of portions of utensils, a mapping service to look up a restaurant, an eating schedule, an eating time, ambient audio to determine co-presence of others who are eating, a blood sugar level, motion data, or a database of coordinates of restaurants. In this example, computing device 4 inputs the computer-generated indication into a trained classifier, performs a classification and provides an outputted value. The outputted value (e.g., a number) may represent a probability, a distance measure between the data and a hyper-surface, or some other type of data that indicates how close, or otherwise similar, the computer-generated indication may be to the pre-defined activity data 15. Computing device 4 may compare the number to a threshold to determine a correlated confidence, which computing device 4 may use to determine whether the user is currently consuming an ingestible substance. For instance, if the correlated confidence is strong or high enough (i.e., above a confidence threshold), the computing device may determine that the user is currently consuming an ingestible substance.

In still other examples, to determine whether the user is currently consuming an ingestible substance, activity detection module 10 may determine a degree of confidence between the pre-defined activity data 15 and the at least one computer-generated indication. A degree of confidence in some examples may be a particular value that indicates how likely it is that the user is consuming an ingestible substance. For instance, based on the comparison between the pre-defined activity data 15 and the at least one computer-generated indication, activity detection module 10 may determine a degree of confidence that represents a likelihood that the computer-generated indication indicates the user is currently consuming the ingestible substance. Activity detection module 10 may compare the degree of confidence to a threshold, which may be stored in data storage 14. If activity detection module 10 determines that the degree of confidence satisfies (e.g., is above) the threshold, activity detection module 10 may send the indication to I/O module 12 that indicates the user is currently consuming the ingestible substance. On the other hand, in some examples, if activity detection module 10 determines that the degree of confidence is below the threshold, activity detection module 10 may send an indication to I/O module 12 that indicates the user is not currently consuming the ingestible substance. In some examples of the indication indicating that the user is not currently consuming the ingestible substance, activity detection module 10 may do nothing. Responsive to determining that the user is currently consuming the ingestible substance, activity detection module 10 may send an indication to I/O module 12 that indicates the user is currently consuming the ingestible substance.

Responsive to receiving the indication that user 18 is eating, I/O module 12 may output, via UID 6, a reminder 26 to consume at least one particular ingestible substance. Generally, a reminder may be any visual, audio, haptic, or electronic stimulus provided by computing device 4. In some examples, reminder 26 may be a text message, an email, or some other visual reminder that is displayed on UID 6 and provided by computing device 4. As described above, user 18 may have a condition such as arthritis. In order to treat the user's arthritis, user 18 may have a prescription of hydrocortisone, a medication that can cause nausea-type side-effects if taken without food. Responsive to computing device 4 recognizing that user 18 is eating spaghetti and meatballs 20, I/O module 12 of computing device 4 may output, via UID 6, reminder 26 to remind the user that they must take the prescribed two tablets of hydrocortisone. In some examples, I/O module 12 may output reminders as other visual, haptic, audio, or electronic stimuli. Examples of such reminders may include, but are not limited to vibration on a watch, UI element for display, sound from speakers mounted on computing device 4, neural stimulation, sound sent to a computing device different from computing device 4, or flashing lights mounted on computing device 4, to name only a few examples.

In some examples, I/O module 12 may output reminder 26 immediately after determining that user 18 is eating. In some examples, I/O module 12 may output reminder 26 prior to user 18 beginning to eat (e.g., based on determining from a picture of utensils, a location of the environment, a dinner calendar event, and/or other data indicative that a user will begin eating). In some examples, I/O module 12 may output reminder 26 at some time after or before the user 18 is eating, such as thirty minutes later or one hour later. In some examples, I/O module 12 may, responsive to an indication of user input, output a second reminder some amount of time after outputting the first reminder, such as five minutes later or ten minutes later.

Techniques according to this disclosure may include a "snooze" function. The snooze function may remind the user again at some time after the first reminder if they are unable to take the suggested particular ingestible substance right away. I/O module 12 may also wait until computing device 4 determines that user 18 is no longer eating (i.e., the computer-generated indication no longer matches the pre-defined activity data) and output reminder 26 at that time.

By determining whether a user is currently consuming an ingestible substance and, based on that determination, outputting a reminder to consume a particular ingestible substance (i.e., a medication), computing device 4 may notify a user to take her prescribed medication in a more efficient and beneficial manner. If a medication must be taken with food, a reminder at a specific time or when a user is at a specific location may not provide the user with the most beneficial alert. By generating indications and comparing the computer-generated indications to pre-defined activity data 15 that is indicative of a user eating, computing device 4 may determine an approximate time when a user is actually eating food, and provide the reminder based on that determination. By providing more prompt and beneficial reminders, a user may miss fewer dosages of medication and may take their prescribed medication in the most effective time frame, reducing possible side-effects from missing dosages, taking a dosage at the wrong time, or taking a dosage without the necessary food intake recommended for the medication. For example, if a medication is supposed to be taken with food and it is taken without food, nausea or vomiting may occur in a patient. Further, the medication may not be absorbed into the body, as some medications require being mixed with food or fat in order to be processed.

Throughout the disclosure, examples are described where a computing device and/or a computing system may analyze information (e.g., locations, speeds, etc.) associated with a computing device only if the computing device receives permission from the user to analyze the information. For example, in situations discussed below in which the computing device may collect or may make use of information associated with the user, the user may be provided with an opportunity to provide input to control whether programs or features of the computing device can collect and make use of user information (e.g., information about a user's current location, current speed, etc.), or to dictate whether and/or how to the computing device may receive content that may be relevant to the user. In addition, certain data may be treated in one or more ways before it is stored or used by the computing device and/or computing system, so that personally-identifiable information is removed. For example, a user's identity may be treated so that no personally identifiable information can be determined about the user, or a user's geographic location may be generalized where location information is obtained (such as to a city, ZIP code, or state level), so that a particular location of a user cannot be determined. Thus, the user may have control over how information is collected about the user and used by the computing device.

Figure 2:
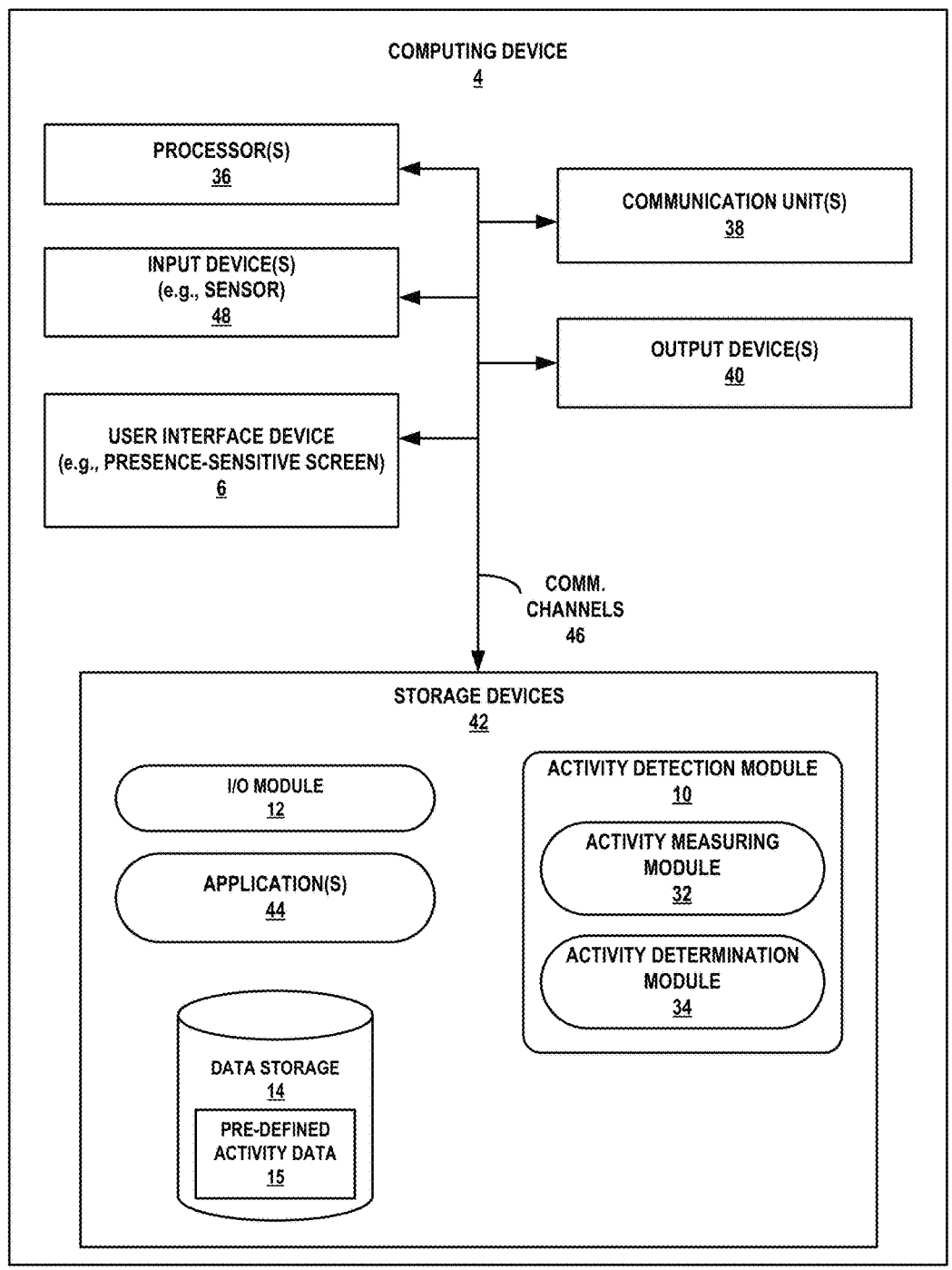
FIG. 2 is a block diagram illustrating an example computing device, in accordance with one or more aspects of the present disclosure.

FIG. 2 is a block diagram illustrating an example computing device, in accordance with one or more aspects of the present disclosure. Computing device 4 of FIG. 2 is described below within the context of FIG. 1. FIG. 2 illustrates only one particular example of computing device 4, and many other examples of computing device 4 may be used in other instances and may include a subset of the components included in example computing device 4 or may include additional components not shown in FIG. 2.

As shown in the example of FIG. 2, computing device 4 includes UID 6, one or more processors 36, one or more input devices 48, one or more communication units 38, one or more output devices 40, and one or more storage devices 42. In the illustrated example, storage devices 42 of computing device 4 also include I/O module 12, activity detection module 10, data storage 14, and one or more applications 44. Activity detection module 10 includes activity measuring module 32 ("AM module 32") and activity determination module 34 ("AD module 34"). Communication channels 46 may interconnect each of the components 6, 10, 12, 14, 32, 34, 36, 38, 40, 42, 44, and 48 for inter-component communications (physically, communicatively, and/or operatively). In some examples, communication channels 46 may include a system bus, a network connection, an inter-process communication data structure, or any other method for communicating data.

One or more input devices 48 of computing device 4 may receive input. Examples of input are tactile, audio, video, and sensor input. Input devices 48 of computing device 4, in some examples, include a presence-sensitive input device (e.g., a touch sensitive screen, a presence-sensitive display), mouse, keyboard, voice responsive system, video camera, microphone, or any other type of device for detecting input from a human or machine. Input devices 42 may include the one or more sensors 8, as described with respect to FIG. 1. In some examples, input devices 42 include physiological sensors for obtaining physiological parameter information associated with a user of computing device 10. For example, input devices 42 may include a heart monitor sensor, a temperature sensor, a galvanic skin response sensor, an accelerometer, a gyroscope, a pressure sensor, a blood pressure sensor, and/or any other sensor for measuring a physiological parameter that computing device 4 may use for determining a physiological condition of a user, such as any of the one or more sensors 8 described above with respect to FIG. 1.

One or more output devices 40 of computing device 4 may generate output. Examples of output are tactile, audio, and video output. Output devices 40 of computing device 4, in some examples, include a presence-sensitive display, sound card, video graphics adapter card, speaker, cathode ray tube (CRT) monitor, liquid crystal display (LCD), or any other type of device for generating output to a human or machine. Output devices 40 may output an audio reminder to consume at least one particular ingestible substance, such as a medication. Output devices 40 may also output a textual reminder on computing device 4 to consume at least one particular ingestible substance, such as a medication. In some examples, output devices 40 may send, via a wireless connection such as Bluetooth®, GPS, 3G, 4G, and Wi-Fi® radios, a reminder to consume at least one particular ingestible substance, such as a medication, to a secondary computing device, such as a text message or an email reminder.

One or more communication units 38 of computing device 4 may communicate with external devices via one or more networks by transmitting and/or receiving network signals on the one or more networks. For example, computing device 4 may use communication unit 38 to transmit and/or receive radio signals on a radio network such as a cellular radio network. Likewise, communication units 38 may transmit and/or receive satellite signals on a satellite network such as a GPS network. Examples of communication unit 38 include a network interface card (e.g. such as an Ethernet card), an optical transceiver, a radio frequency transceiver, a GPS receiver, or any other type of device that can send and/or receive information. Other examples of communication units 38 may include Bluetooth®, GPS, 3G, 4G, and Wi-Fi® radios found in mobile devices as well as Universal Serial Bus (USB) controllers.

In some examples, UID 6 of computing device 4 may include functionality of input devices 48 and/or output devices 40. In the example of FIG. 2, UID 6 may be or may include a presence-sensitive input device. In some examples, a presence-sensitive input device may detect an object at and/or near the presence-sensitive input device. As one example range, a presence-sensitive input device may detect an object, such as a finger or stylus that is within two inches or less of the presence-sensitive input device. In another example range, a presence-sensitive input device may detect an object six inches or less from the presence-sensitive input device, and other ranges are also possible. The presence-sensitive input device may determine a location (e.g., an (x,y) coordinate) of the presence-sensitive input device at which the object was detected. The presence-sensitive input device may determine the location selected by the input device using capacitive, inductive, and/or optical recognition techniques. In some examples, presence-sensitive input device provides output to a user using tactile, audio, or video stimuli as described with respect to output device 40, and may be referred to as a presence-sensitive display.

While illustrated as an internal component of computing device 4, UID 6 also represents an external component that shares a data path with computing device 4 for transmitting and/or receiving input and output. For instance, in one example, UID 6 represents a built-in component of computing device 4 located within and physically connected to the external packaging of computing device 4 (e.g., a screen on a mobile phone or wearable computing device). In another example, UID 6 represents an external component of computing device 4 located outside and physically separated from the packaging of computing device 4 (e.g., a monitor, a projector, etc. that shares a wired and/or wireless data path with computing device 4).

One or more storage devices 42 within computing device 4 may store information for processing during operation of computing device 4. In some examples, storage device 42 is a temporary memory, meaning that a primary purpose of storage device 42 is not long-term storage. Storage devices 42 on computing device 10 may configured for short-term storage of information as volatile memory and therefore not retain stored contents if powered off. Examples of volatile memories include random access memories (RAM), dynamic random access memories (DRAM), static random access memories (SRAM), and other forms of volatile memories known in the art.

Storage devices 42, in some examples, also include one or more computer-readable storage media. Storage devices 42 may be configured to store larger amounts of information than a temporary memory. Storage devices 42 may further be configured for long-term storage of information as non-volatile memory space and retain information after power on/off cycles. Examples of non-volatile memories include magnetic hard discs, optical discs, floppy discs, flash memories, or forms of electrically programmable memories (EPROM) or electrically erasable and programmable (EEPROM) memories. Storage devices 42 may store program instructions and/or data associated with activity detection module 10, I/O module 12, AM module 32, AD module 34, and one or more applications 44.

In some examples, data storage 14 is a temporary memory, meaning that a primary purpose of data storage 14 is not long-term storage. Data storage 14 on computing device 4 may configured for short-term storage of information as volatile memory and therefore not retain stored contents if powered off. Examples of volatile memories include random access memories (RAM), dynamic random access memories (DRAM), static random access memories (SRAM), and other forms of volatile memories known in the art.

Data storage 14, in some examples, also includes one or more computer-readable storage media. Data storage 14 may be configured to store larger amounts of information than volatile memory. Data storage 14 may further be configured for long-term storage of information as non-volatile memory space and retain information after power on/off cycles. Examples of non-volatile memories include magnetic hard discs, optical discs, floppy discs, flash memories, or forms of electrically programmable memories (EPROM) or electrically erasable and programmable (EEPROM) memories. Data storage 14 may store program instructions and/or data associated with activity detection module 10, I/O module 12, UID 6, and sensors 8.

Data storage 14, in some examples, may also be long-term storage and may be implemented in a number of different forms including data storage files, or as a database management system (DBMS). The database management system may be a relational (RDBMS), hierarchical (HDBMS), multidimensional (MDBMS), object oriented (ODBMS or OODBMS) or object relational (ORDBMS), or other database management system. Furthermore, although illustrated separately, data storage 14 could be combined into a single database or other data storage structure. Data storage 14 could, for example, be implemented as a single relational database (such as that marketed by Microsoft® Corporation under the trade designation 'SQL SERVER").

One or more processors 36 may implement functionality and/or execute instructions within computing device 4. For example, processors 36 on computing device 4 may receive and execute instructions stored by storage devices 42 that execute the functionality of activity detection module 10, I/O module 12, AM module 32, AD module 34, and one or more applications 44. These instructions executed by processors 36 may cause computing device 4 to store information within storage devices 42 during program execution. Processors 36 may execute instructions of activity detection module 10, I/O module 12, AM module 32, AD module 34, and one or more applications 44 to cause output devices 40 to output one or more reminders based on activity data received by computing device 4. That is, activity detection module 10, I/O module 12, AM module 32, AD module 34, and one or more applications 44 may be operable by processors 36 to perform various actions, including outputting information associated with a reminder to consume at least one particular ingestible substance via UID 6 or output devices 40.

In accordance with one or more aspects of this disclosure, I/O module 12 may receive at least one computer-generated indication from input devices 48. Activity detection module 10, which includes activity measuring module 32 (AM module 32) and activity determination module 34 (AD module 34), may use the at least one computer-generated indication to determine whether a user is currently consuming an ingestible substance.

AM module 32 may initially receive the at least one computer-generated indication from I/O module 12 and perform computations on the at least one computer-generated indication. For example, as described in the example of FIG. 1, the at least one computer-generated indication could be motion information corresponding to user's arm 19 moving fork 24 from plate 22B to the user's mouth. AM module 32 may take that motion information and convert it into one or more motion vectors. In another example, the activity data may be a change in blood sugar level. AM module 32 may perform calculations on the change in blood sugar level to determine how much the blood sugar level changed and a rate at which the blood sugar level changed.

In some examples, AM module 32 may receive a computer-generated indication without performing calculations or transformations on the at least one computer-generated indication, such as a picture of food, a picture of utensils, motion data obtained from one or more sensors, a blood sugar level, a time, a sound, a picture of a cheekbone, or GPS coordinates. AM module 32 may transfer this computer-generated indication to AD module 34.

AD module 34 may determine, based at least in part on the at least one computer-generated indication and pre-defined activity data 15 that are indicative of an act of a human consuming an ingestible substance, whether the user is currently consuming an ingestible substance. Pre-defined activity data 15 may be at least one of image data of portions of food, a motion profile, image data of portions of a cheekbone, image data of portions of utensils, a mapping service to look up a restaurant, an eating schedule, an eating time, ambient audio to determine co-presence of others who are eating, a blood sugar level, motion data, a database of coordinates of restaurants, and a trained classifier. In some examples, AD module 34 may determine whether the user is currently consuming an ingestible substance, such as food, by a simple comparison of the computer-generated indication and the pre-defined activity data 15.

In the example where the pre-defined activity data 15 is image data of portions of food, image data of portions of utensils, or image data of eating environments (e.g., dining rooms, restaurants, kitchens, etc.), the computer-generated indication may be a picture of food, and AD module 34 may determine that a user is currently consuming an ingestible substance by comparing color information, texture information, and/or shape information to a stored picture of different types of food, utensils, and/or eating environments. In the example where the pre-defined activity data 15 is a motion profile or motion data, the computer-generated indication may be motion data, and AD module 34 may determine that a user is currently consuming an ingestible substance by comparing the length of motion, the speed of motion, the rotations involved in the motion, and the consistency of the motion to the motion profile.

In the example where the pre-defined activity data 15 is image data of portions of a cheekbone, the computer-generated indication may be a picture of a user's cheekbone, and AD module 34 may determine that a user is currently consuming an ingestible substance by comparing shape information, size information, and how the pictures change over a period of time, which may indicate a motion of the cheekbone. In the example where the pre-defined activity data 15 is a mapping service to look up a restaurant or a database of coordinates of restaurants, the computer-generated indication may be GPS coordinates, and AD module 34 may determine that a user is currently consuming an ingestible substance by comparing the location of the user and the location of the known restaurant.

In the example where the pre-defined activity data 15 is an eating schedule or an eating time, the computer-generated indication may be a time, and AD module 34 may determine that a user is currently consuming an ingestible substance by comparing a current time with the times defined in the eating schedule to determine a temporal distance. For instance, some medications may only need to be taken with a particular meal, such as breakfast, lunch, or dinner. Therefore, even though a user may be eating, if the time does not match the required time, computing device 4 may not output the reminder, as the eating schedule and/or eating time may not match the current time.

In the example where the pre-defined activity data 15 is ambient audio to determine co-presence of others who are eating, the computer-generated indication may be a sound, and AD module 34 may determine that a user is currently consuming an ingestible substance by comparing various characteristics of the computer-generated indication to corresponding characteristics of the pre-defined ambient audio, such as pitch, tone, and volume, among other things.

In the example where the pre-defined activity data 15 is a blood sugar level, the computer-generated indication may be a change in blood sugar level, and AD module 34 may determine that a user is currently consuming an ingestible substance by comparing the change in blood sugar level to a typical change in blood sugar levels that one may see when eating. Further, pre-defined activity data 15 could be any combination of the above-listed instances of pre-defined activity data 15, and the computer-generated indications may be any combination of the above-listed instances of computer-generated indications.

In some examples, such as the example where the pre-defined activity data 15 comprises at least a trained classifier, AD module 34 may train a classifier using a process such as Neural Network or Support Vector Machine (SVM). AD module 34 may train the classifier based on any of the other aforementioned pre-defined activity data alone or in combination, such as image data of portions of food, a motion profile, image data of portions of a cheekbone, image data of portions of utensils, a mapping service to look up a restaurant, an eating schedule, an eating time, ambient audio to determine co-presence of others who are eating, a blood sugar level, motion data, or a database of coordinates of restaurants. In this example, AD module 34 inputs the computer-generated indication into an algorithm that is based on the trained classifier and the process used to train the classifier, the product of which may be a number. The number may represent a probability, a distance measure between the data and a hyper-surface, or some other type of data that indicates how close the computer-generated indication may be to the pre-defined activity data 15. AD module 34 may then threshold the number to determine a correlated confidence, from which AD module 34 may determine whether the user is currently consuming an ingestible substance. For instance, if the correlated confidence is strong or high enough (i.e., above a confidence threshold), AD module 34 may determine that the user is currently consuming an ingestible substance.

In some examples, AD module 34 may determine whether the user is currently consuming an ingestible substance by determining a degree of confidence between the pre-defined activity data 15 and the at least one computer-generated indication that indicates whether the user is currently consuming the ingestible substance. Once a degree of confidence is determined, AD module 34 may compare the degree of confidence to a threshold to determine whether the user is currently consuming an ingestible substance, where the threshold may be pre-defined. Responsive to determining that the degree of confidence satisfies the threshold, AD module 34 may determine that the user is currently consuming the ingestible substance. In some examples, if the degree of confidence is greater than the threshold, AD module 34 will determine that the user is consuming an ingestible substance. In some examples, if the degree of confidence is greater than or equal to the threshold, AD module 34 will determine that the user is consuming an ingestible substance.

In some examples, AD module 34 may determine whether the user is currently consuming an ingestible substance based on two or more computer-generated indications and two or more sets of pre-defined activity data. Although this example is described with respect to two computer-generated indications and two sets of pre-defined activity data, this example could be implemented with more than two computer-generated indications and two sets of pre-defined activity data or with only one computer-generated indication and pre-defined activity data. AD module 34 may determine a first difference between the first computer-generated indication and first pre-defined activity data. AD module 34 may determine a second difference between the second computer-generated indication and second pre-defined activity data. AD module 34 may apply a first weight, corresponding to the first computer-generated indication, to the first difference to generate a first weighted difference value. AD module 34 may apply a second weight, corresponding to a second computer-generated indication, to the second difference to generate a second weighted difference value. AD module 34 may aggregate the first and second weighted difference values to determine an aggregated weighted difference value. AD module 34 may determine, based at least in part on the aggregated weighted difference value, whether the user is currently consuming the ingestible substance.

AD module 34 may further implement machine-learning capabilities in computing device 4. For example, responsive to determining that the user is currently consuming an ingestible substance, AD module 34 of computing device 4 may generate one or more difference values between the at least one computer-generated indication and the pre-defined activity data 15. For instance, if the computer-generated indication includes vectors of motion data, the difference values may be a difference of position, magnitude, and speed between the measured activity data and the pre-defined activity data 15. AD module 34 may update the pre-defined activity data 15 based on the one or more difference values, storing them in data storage 14. In future instances of computing device 4 determining whether a user is currently consuming an ingestible substance, AD module 34 may determine whether the user is currently consuming an ingestible substance based at least in part on the at least one computer-generated indication and the updated pre-defined activity data 15. For example, when considering the pre-defined motion data that indicates that a user is currently consuming an ingestible substance, AD module 34 may adjust the pre-defined motion data according to the aggregated one or more difference values and use the resulting data to determine whether a user us currently consuming an ingestible substance, in accordance with the methods described above. In the examples where the pre-defined activity data 15 includes a trained classifier, the trained classifier may be updated and re-trained based on the computer-generated indications.

Figure 3:
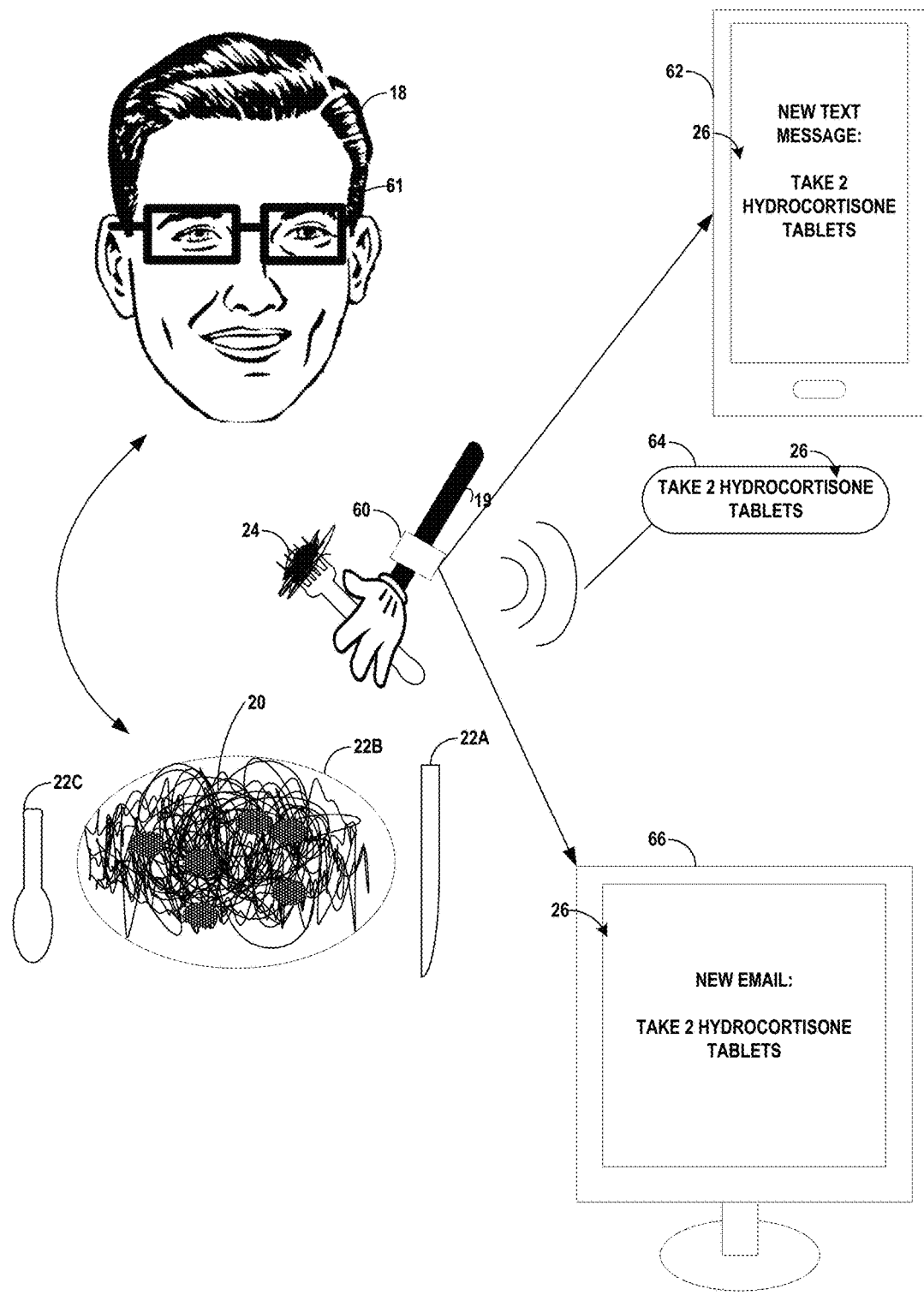
FIG. 3 is a conceptual diagram illustrating an example system including a computing device that determines whether a user is consuming an ingestible substance and outputs a reminder to consume at least one particular ingestible substance, in accordance with one or more aspects of the present disclosure.

FIG. 3 is a conceptual diagram illustrating an example system including a computing device that determines whether a user is consuming an ingestible substance and outputs a reminder to consume at least one particular ingestible substance to be displayed on a second computing device, in accordance with one or more aspects of the present disclosure. In the example of FIG. 3, user 18 may be wearing computing device 60, which may be functionally and structurally similar to computing device 4 of FIG. 1. Further, user 18 may be wearing computing device 61, which may be functionally and structurally similar to computing device 5 of FIG. 1.

In the example of FIG. 3, computing device 60 and/or computing device 61 may determine that user 18 is eating an ingestible substance, such as spaghetti and meatballs 20, using any of the techniques described above with respect to FIGS. 1 and/or 2. Responsive to determining that the user is currently consuming the ingestible substance, computing device 60 and/or computing device 61 may output a reminder 26 to consume at least one particular ingestible substance, such as a medication like hydrocortisone. As shown in the example of FIG. 3, in some examples, computing device 60 and/or computing device 61 may output reminder 26 in such a way that reminder 26 is not a visual reminder on a user-interface display of computing device 60 and/or computing device 61.

For example, computing device 60 and/or computing device 61 may output reminder 26 as audio data 64. For instance, computing device 60 and/or computing device 61 may output reminder 26 as audio data 64 from speakers in computing device 60 and/or computing device 61, or computing device 60 and/or computing device 61 may output reminder 26 as audio data 64 in a separate computing device coupled to computing device 60 and/or computing device 61, either wired or wirelessly. In some examples, user 18 may be able to customize different aspects of audio output 64, such as the tone, the volume, the pitch, the rhythm, the speed, or the voice. In some examples, computing device 60 and/or computing device 61 may output reminder 26 as a visual reminder. For example, computing device 60 and/or computing device 61 may output reminder 26 as a text message 62. In yet another example, computing device 60 and/or computing device 61 may output reminder 26 as an email message 66. In some examples, computing device 60 and/or computing device 61 may output reminder 26 to a pills box.

Figure 4:
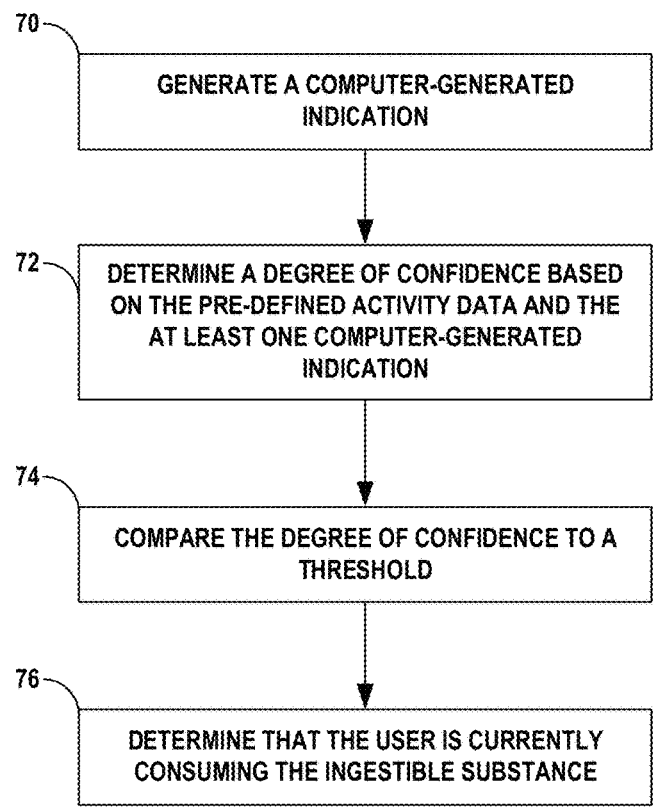
FIG. 4 is a flow diagram illustrating example operations of a computing device that implements techniques for determining whether a user is consuming an ingestible substance, in accordance with one or more aspects of the present disclosure.
Figure 5:
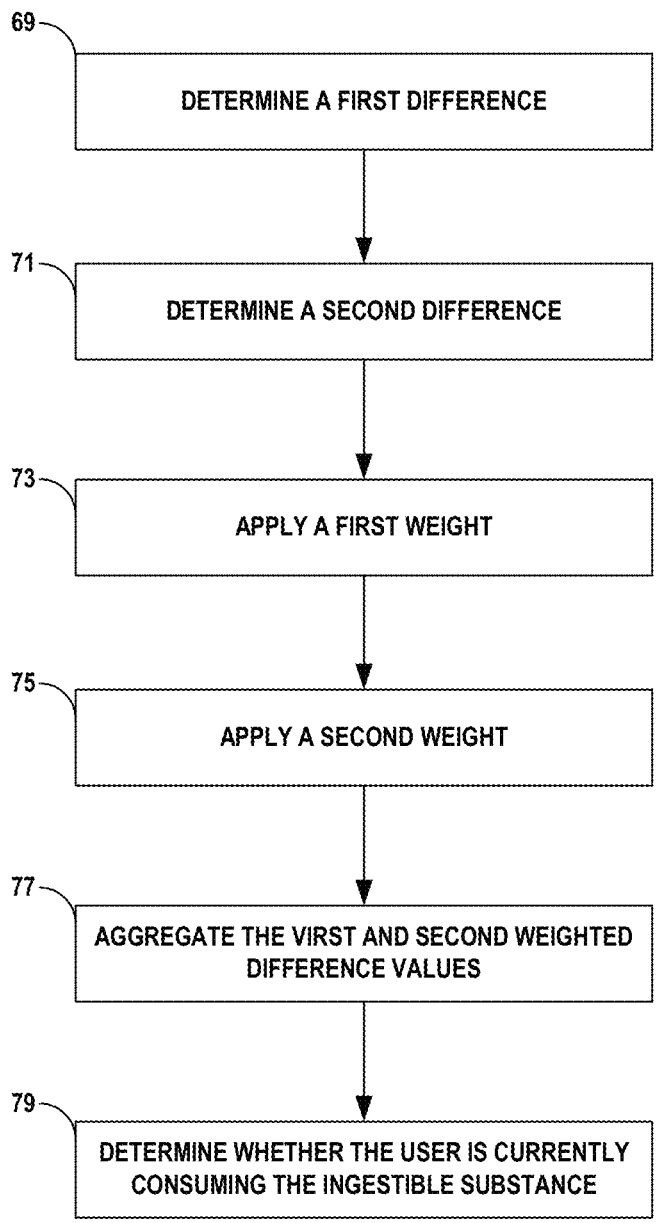
FIG. 5 is a flow diagram illustrating example operations of a computing device that implements techniques for determining whether a user is consuming an ingestible substance, in accordance with one or more aspects of the present disclosure.
Figure 6:
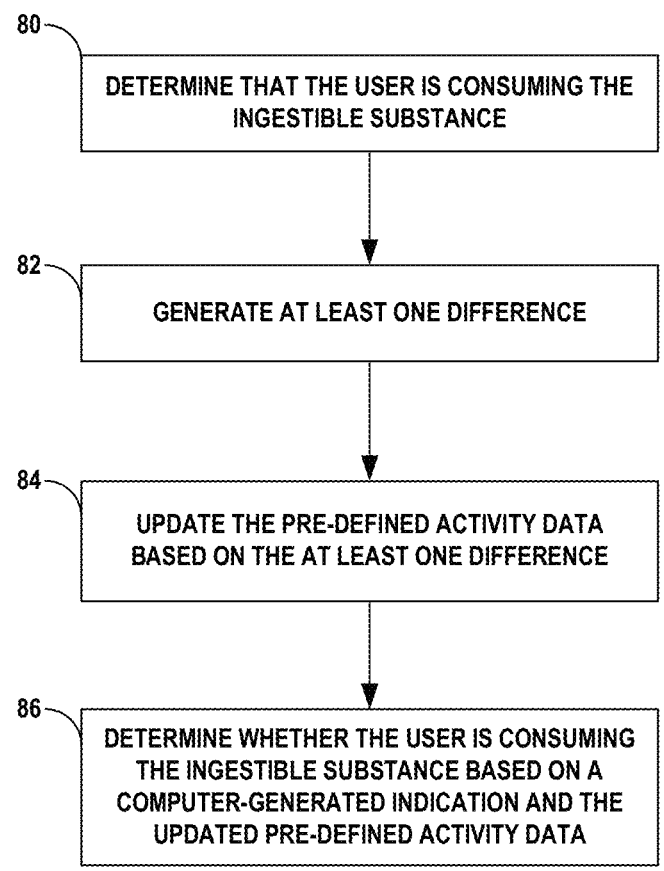
FIG. 6 is a flow diagram illustrating example operations of a computing device that implements techniques for determining whether a user is consuming an ingestible substance, in accordance with one or more aspects of the present disclosure.

FIGS. 4-6 are flow diagrams illustrating example operations of a computing device that implements techniques of determining whether a user is consuming an ingestible substance, in accordance with one or more aspects of the present disclosure. For purposes of illustration only, the example operations are described below within the context of computing device 4, as shown in FIGS. 1 and 2.

In the particular example of FIG. 4, the flow diagram illustrates how computing device 4 may determine whether a user, such as user 18, is currently consuming an ingestible substance. Computing device 4 may generate at least one computer-generated indication (70). The at least one computer-generated indication may be at least one of a picture of food, a picture of utensils, motion data obtained from the one or more sensors, a blood sugar level, a time, a sound, a picture of a cheekbone, and GPS coordinates.

Computing device 4 may determine a degree of confidence based at least in part on the pre-defined activity data and the at least one computer-generated indication, a degree of confidence that indicates a confidence that the user is currently consuming the ingestible substance (72). In some examples, the pre-defined activity data may be at least one of image data of portions of food, a motion profile, image data of portions of a cheekbone, image data of portions of utensils, a mapping service to look up a restaurant, an eating schedule, an eating time, ambient audio to determine co-presence of others who are eating, a blood sugar level, motion data, a database of coordinates of restaurants, and a trained classifier. For instance, the degree of confidence may be a confidence that indicates whether the user is currently consuming the ingestible substance. As one example, the degree of confidence may indicate a likelihood that the computer-generated indication indicates that the user is currently consuming an ingestible substance.

In some examples, degree of confidence may be based on the degree of similarity between the computer-generated indication and pre-defined activity data. For instance, if a portion of an image in the computer-generated indication is nearly identical to image data in the pre-defined activity data, the degree of similarity may be high and therefore the degree of confidence may be high. Conversely, if a portion of an image in the computer-generated indication is nearly completely difference than the image data in the pre-defined activity data, the degree of similarity may be low and therefore the degree of confidence may be low. While described with respect to a computer-generated indication that is a portion of an image, the degree of confidence may be computed for other computer-generated indications by determining the degree of similarity between the computer-generated indication and the pre-defined activity data (e.g., distance between locations, similarity between blood sugar measurements, similarity between measured motion data and motion data in pre-defined activity, to name only a few examples).

Computing device 4 may compare the degree of confidence to a threshold to determine whether the degree of confidence satisfies the threshold (74). Computing device 4 may determine, based at least in part on a comparison between the threshold and the degree of confidence, that the user is currently consuming the ingestible substance (76). For instance, if the degree of confidence is greater than the threshold, computing device 4 may determine that the user is current consuming the ingestible substance and output reminder 26 to consume at least one particular ingestible substance. If the degree of confidence is less than the threshold, computing device 4 may determine that the user is not currently consuming the ingestible substance and do nothing.

In the particular example of FIG. 5, the flow diagram illustrates how computing device 4 may determine when the user is consuming an ingestible substance based on multiple computer-generated indications and multiple sets of pre-defined activity data. Although this example is described with respect to two computer-generated indications and two sets of pre-defined activity data, this example could be implemented with more than two computer-generated indications and two sets of pre-defined activity data or with only one computer-generated indication and pre-defined activity data.

Computing device 4 may determine a first difference between the computer-generated indication and first pre-defined activity data (69). Computing device 4 may determine a second difference between a second computer-generated indication and second pre-defined activity data (71). In some examples, these differences may be a result of any of the comparisons described with respect to FIG. 1.

Computing device 4 may apply a first weight, corresponding to the first computer-generated indication, to the first difference to generate a first weighted difference value (73). Computing device 4 may also apply a second weight, corresponding to a second computer-generated indication, to the second difference to generate a second weighted difference value (75). In these steps, computing device 4 may determine the weighted difference values by taking a weight and multiplying it by a difference between the computer-generated indication and the pre-define activity data.

Computing device 4 may aggregate the first and second weighted difference values to generate an aggregated weighted difference value (77). Computing device 4 may determine, based at least in part on the aggregated weighted difference value, whether the user is currently consuming the ingestible substance (79). Computing device 4 may determine whether the user is currently consuming the ingestible substance by comparing the aggregated weighted difference value to a pre-defined threshold value, and determining that the user is currently consuming the ingestible substance if the aggregated weighted difference value is less than the threshold value. If computing device 4 determines that the user is currently consuming the ingestible substance, computing device 4 may output reminder 26 to consume at least one particular ingestible substance. Otherwise, computing device 4 may determine that the user is not currently consuming the ingestible substance and do nothing.

In some examples, explicit weights are not assigned to difference values. In some examples, where the pre-defined activity data includes a trained classifier, the trained classifier may inherently include weights or some descriptor that defines how heavily to weigh particular data points. As described in FIG. 1, in some examples, such as where the pre-defined activity data comprises at least a trained classifier, comparisons may not be made. Instead, computing device 4 may train a classifier using a process such as Neural Network or Support Vector Machine (SVM). Computing device 4 may train the classifier based on any of the other aforementioned pre-defined activity data alone or in combination, such as image data of portions of food, a motion profile, image data of portions of a cheekbone, image data of portions of utensils, a mapping service to look up a restaurant, an eating schedule, an eating time, ambient audio to determine co-presence of others who are eating, a blood sugar level, motion data, or a database of coordinates of restaurants.

As an example, computing device 4 inputs the computer-generated indication into a trained classifier, performs a classification and provides an outputted value. The outputted value (e.g., a number) may represent a probability, a distance measure between the data and a hyper-surface, or some other type of data that indicates how close, or otherwise similar, the computer-generated indication may be to the pre-defined activity data. Computing device 4 may compare the number to a threshold to determine a correlated confidence, which computing device 4 may use to determine whether the user is currently consuming an ingestible substance. For instance, if the correlated confidence is strong or high enough (i.e., above a confidence threshold), the computing device may determine that the user is currently consuming an ingestible substance.

In the particular example of FIG. 6, the flow diagram illustrates how computing device 4 may learn a user's habits and more closely determine when the user is consuming an ingestible substance. Computing device 4 may determine that the user is currently consuming an ingestible substance (80). Computing device 4 may determine this by using any of the techniques described above, including the technique of FIG. 4 or FIG. 5.

Responsive to determining that the user is currently consuming the ingestible substance, computing device 4 may generate at least one difference between the at least one computer-generated indication and the pre-defined activity data (82). For example, computing device 4 may find a difference between the value and the expected value, as described in FIG. 4.

Computing device 4 may update the pre-defined activity data based on the at least one difference (84). Using these updates, in a future instance of when computing device 4 is determining whether the user is currently consuming an ingestible substance, computing device 4 may determine whether the user is currently consuming an ingestible substance based at least in part on the at least one computer-generated indication and the updated pre-defined activity data (86).

Figure 7:
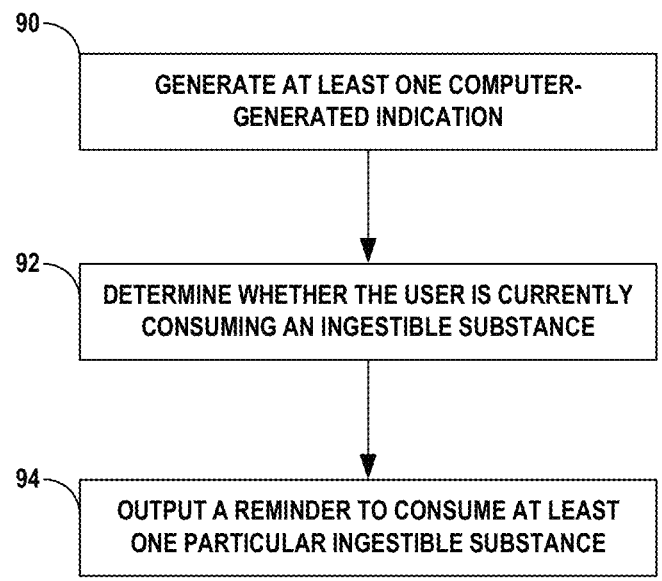
FIG. 7 is a flowchart illustrating example operations of a computing device that implements techniques for determining whether a user is consuming an ingestible substance and outputting a reminder to consume at least one particular ingestible substance, in accordance with one or more aspects of the present disclosure.

FIG. 7 is a flowchart illustrating example operations of a computing device that implements techniques for determining whether a user is consuming an ingestible substance and outputting a reminder to consume at least one particular ingestible substance, in accordance with one or more aspects of the present disclosure. For purposes of illustration only, the example operations are described below within the context of computing device 4, as shown in FIGS. 1 and 2.

In the particular example of FIG. 7, computing device 4 may generate at least one computer-generated indication (90). The at least one computer-generated indication, in some examples, may be at least one of a picture of food, a picture of utensils, motion data obtained from one or more sensors, a blood sugar level, a time, a sound, a picture of a cheekbone, and GPS coordinates.

Computing device 4 may determine whether the user is currently consuming an ingestible substance based at least in part on the at least one computer-generated indication and pre-defined activity data that are indicative of an act of a human consuming an ingestible substance (92). In some examples, computing device 4 may implement the techniques of FIGS. 1, 2, 4, 5, and/or 6 to determine whether the user is currently consuming an ingestible substance. The pre-defined activity data, in some examples, may be at least one of image data of portions of food, a motion profile, image data of portions of a cheekbone, image data of portions of utensils, a mapping service to look up a restaurant, an eating schedule, an eating time, ambient audio to determine co-presence of others who are eating, a blood sugar level, motion data, a database of coordinates of restaurants, and a trained classifier.

Computing device 4 may output a reminder to consume at least one particular ingestible substance responsive to determining that the user is currently consuming an ingestible substance (94). In some examples, such as the example of FIG. 3, the reminder may be at least one of a text message, an email, or an audio message. In some examples, the reminder may be output visually on computing device 4 at UID 6. In this manner, techniques of the disclosure may provide more accurate medication reminders, thereby reducing the number of instances that a user must manually check a computing device to determine whether to ingest medication and potentially saving power and/or reducing wear and tear at the computing device.

Figure 8:
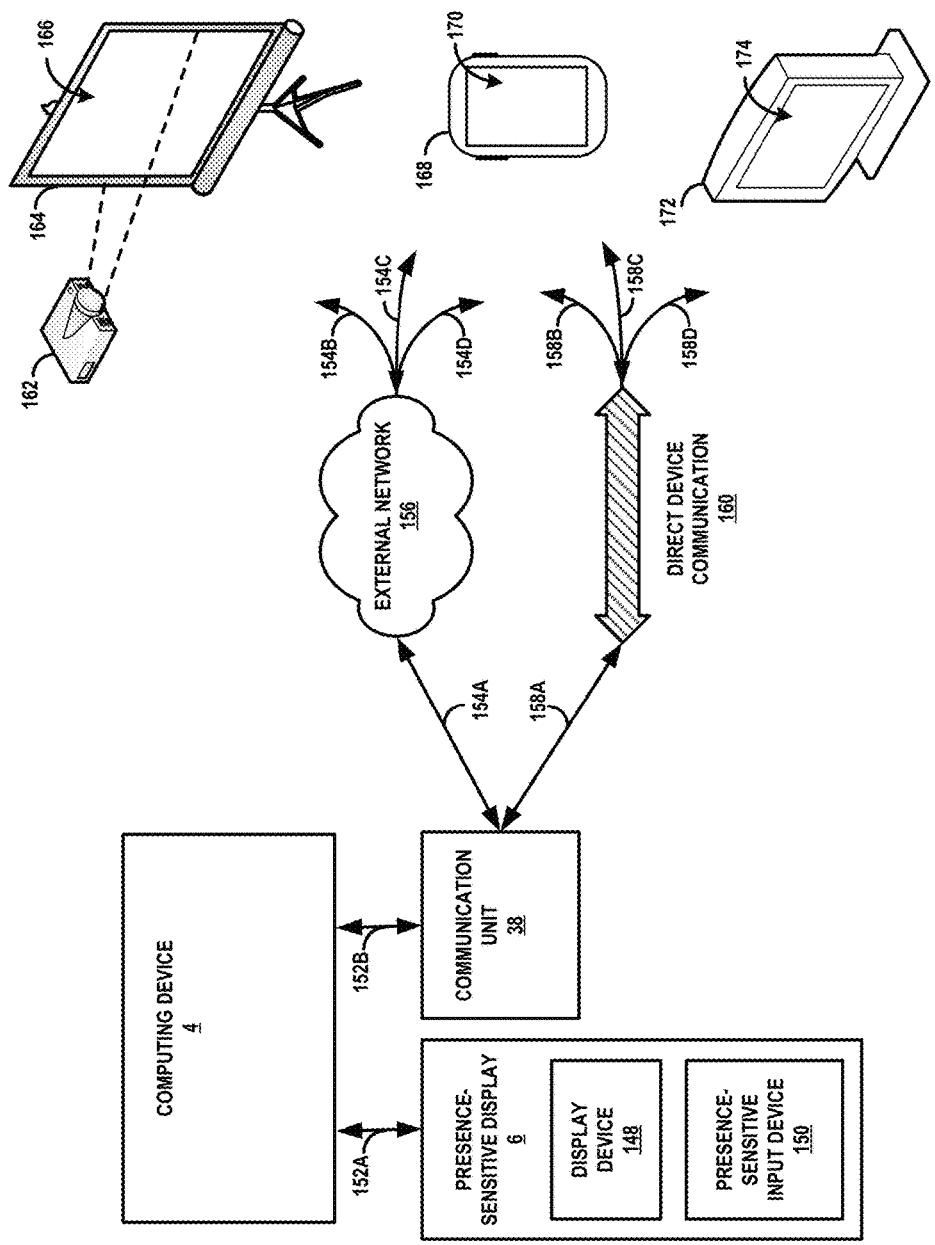
FIG. 8 is a block diagram illustrating an example computing device that outputs graphical content for display at a remote device, in accordance with one or more techniques of the present disclosure.

FIG. 8 is a block diagram illustrating an example computing device that outputs graphical content for display at a remote device, in accordance with one or more techniques of the present disclosure. Graphical content, generally, may include any visual information that may be output for display, such as text, images, a group of moving images, etc. The example shown in FIG. 8 includes a computing device 4, presence-sensitive display 6, communication unit 38, projector 162, projector screen 164, mobile device 168, and visual display device 172. Although shown for purposes of example in FIGS. 1 and 2 as a stand-alone computing device, a computing device such as computing device 4 may, generally, be any component or system that includes a processor or other suitable computing environment for executing software instructions and, for example, need not include a presence-sensitive display.

As shown in the example of FIG. 8, computing device 4 may be a processor that includes functionality as described with respect to processor 36 in FIG. 2. In such examples, computing device 4 may be operatively coupled to presence-sensitive display 6 by a communication channel 152A, which may be a system bus or other suitable connection. Computing device 4 may also be operatively coupled to communication unit 138, further described below, by a communication channel 152B, which may also be a system bus or other suitable connection. Although shown separately as an example in FIG. 8, computing device 4 may be operatively coupled to presence-sensitive display 6 and communication unit 38 by any number of one or more communication channels.

In some examples, such as illustrated previously by computing device 4 in FIGS. 1-2, a computing device may refer to a portable or mobile device such as mobile phones (including smart phones), laptop computers, etc. In some examples, a computing device may be a desktop computers, tablet computers, smart television platforms, cameras, personal digital assistants (PDAs), servers, mainframes, etc.

Presence-sensitive display 6, like presence-sensitive display 4 as shown in FIG. 1, may include display device 148 and presence-sensitive input device 150. Display device 148 may, for example, receive data from computing device 4 and display the graphical content. In some examples, presence-sensitive input device 150 may determine one or more user inputs (e.g., continuous gestures, multi-touch gestures, single-touch gestures, etc.) at presence-sensitive display 6 using capacitive, inductive, and/or optical recognition techniques and send indications of such user input to computing device 4 using communication channel 152A. In some examples, presence-sensitive input device 150 may be physically positioned on top of display device 148 such that, when a user positions an input unit over a graphical element displayed by display device 148, the location at which presence-sensitive input device 150 corresponds to the location of display device 148 at which the graphical element is displayed.

As shown in FIG. 8, computing device 4 may also include and/or be operatively coupled with communication unit 38. Communication unit 38 may include functionality of communication unit 38 as described in FIG. 2. Examples of communication unit 38 may include a network interface card, an Ethernet card, an optical transceiver, a radio frequency transceiver, or any other type of device that can send and receive information. Other examples of such communication units may include Bluetooth, 3G, and WiFi radios, Universal Serial Bus (USB) interfaces, etc. Computing device 4 may also include and/or be operatively coupled with one or more other devices, e.g., input devices, output devices, memory, storage devices, etc. that are not shown in FIG. 8 for purposes of brevity and illustration.

FIG. 8 also illustrates a projector 162 and projector screen 164. Other such examples of projection devices may include electronic whiteboards, holographic display devices, and any other suitable devices for displaying graphical content. Projector 162 and projector screen 164 may include one or more communication units that enable the respective devices to communicate with computing device 4. In some examples, the one or more communication units may enable communication between projector 162 and projector screen 164. Projector 162 may receive data from computing device 4 that includes graphical content. Projector 162, in response to receiving the data, may project the graphical content onto projector screen 164. In some examples, projector 162 may determine one or more user inputs (e.g., continuous gestures, multi-touch gestures, single-touch gestures, etc.) at projector screen using optical recognition or other suitable techniques and send indications of such user input using one or more communication units to computing device 4. In such examples, projector screen 164 may be unnecessary, and projector 162 may project graphical content on any suitable medium and detect one or more user inputs using optical recognition or other such suitable techniques.

Projector screen 164, in some examples, may include a presence-sensitive display 166. Presence-sensitive display 166 may include a subset of functionality or all of the functionality of UI device 4 as described in this disclosure. In some examples, presence-sensitive display 166 may include additional functionality. Projector screen 164 (e.g., an electronic whiteboard), may receive data from computing device 4 and display the graphical content. In some examples, presence-sensitive display 166 may determine one or more user inputs (e.g., continuous gestures, multi-touch gestures, single-touch gestures, etc.) at projector screen 164 using capacitive, inductive, and/or optical recognition techniques and send indications of such user input using one or more communication units to computing device 4.

FIG. 8 also illustrates mobile device 168 and visual display device 172. Mobile device 168 and visual display device 172 may each include computing and connectivity capabilities. Examples of mobile device 168 may include e-reader devices, convertible notebook devices, hybrid slate devices, etc. Examples of visual display device 172 may include other semi-stationary devices such as televisions, computer monitors, etc. As shown in FIG. 3, mobile device 168 may include a presence-sensitive display 170. Visual display device 172 may include a presence-sensitive display 174. Presence-sensitive displays 170, 174 may include a subset of functionality or all of the functionality of presence-sensitive display 4 as described in this disclosure. In some examples, presence-sensitive displays 170, 174 may include additional functionality. In any case, presence-sensitive display 174, for example, may receive data from computing device 4 and display the graphical content. In some examples, presence-sensitive display 174 may determine one or more user inputs (e.g., continuous gestures, multi-touch gestures, single-touch gestures, etc.) at projector screen using capacitive, inductive, and/or optical recognition techniques and send indications of such user input using one or more communication units to computing device 4.

As described above, in some examples, computing device 4 may output graphical content for display at presence-sensitive display 6 that is coupled to computing device 4 by a system bus or other suitable communication channel. Computing device 4 may also output graphical content for display at one or more remote devices, such as projector 162, projector screen 164, mobile device 168, and visual display device 172. For instance, computing device 4 may execute one or more instructions to generate and/or modify graphical content in accordance with techniques of the present disclosure. Computing device 4 may output the data that includes the graphical content to a communication unit of computing device 4, such as communication unit 38. Communication unit 38 may send the data to one or more of the remote devices, such as projector 162, projector screen 164, mobile device 168, and/or visual display device 172. In this way, computing device 4 may output the graphical content for display at one or more of the remote devices. In some examples, one or more of the remote devices may output the graphical content at a presence-sensitive display that is included in and/or operatively coupled to the respective remote devices.

In some examples, computing device 4 may not output graphical content at presence-sensitive display 6 that is operatively coupled to computing device 4. In some examples, computing device 4 may output graphical content for display at both a presence-sensitive display 6 that is coupled to computing device 4 by communication channel 152A, and at one or more remote devices. In such examples, the graphical content may be displayed substantially contemporaneously at each respective device. For instance, some delay may be introduced by the communication latency to send the data that includes the graphical content to the remote device. In some examples, graphical content generated by computing device 4 and output for display at presence-sensitive display 6 may be different than graphical content display output for display at one or more remote devices.

Computing device 4 may send and receive data using any suitable communication techniques. For example, computing device 4 may be operatively coupled to external network 156 using network link 154A. Each of the remote devices illustrated in FIG. 8 may be operatively coupled to network external network 156 by one of respective network links 154B, 154C, and 154D. External network 156 may include network hubs, network switches, network routers, etc., that are operatively inter-coupled thereby providing for the exchange of information between computing device 4 and the remote devices illustrated in FIG. 6. In some examples, network links 154A-154D may be Ethernet, ATM or other network connections. Such connections may be wireless and/or wired connections.

In some examples, computing device 4 may be operatively coupled to one or more of the remote devices included in FIG. 6 using direct device communication 160. Direct device communication 160 may include communications through which computing device 4 sends and receives data directly with a remote device, using wired or wireless communication. That is, in some examples of direct device communication 160, data sent by computing device 4 may not be forwarded by one or more additional devices before being received at the remote device, and vice-versa. Examples of direct device communication 160 may include Bluetooth, Near-Field Communication, Universal Serial Bus, WiFi, infrared, etc. One or more of the remote devices illustrated in FIG. 6 may be operatively coupled with computing device 4 by communication links 158A-158D. In some examples, communication links 158A-158D may be connections using Bluetooth, Near-Field Communication, Universal Serial Bus, infrared, etc. Such connections may be wireless and/or wired connections.

In accordance with techniques of the disclosure, computing device 4 may be operatively coupled to visual display device 172 using external network 156. Computing device 4 may output a graphical keyboard for display at presence-sensitive display 174. For instance, computing device 4 may send data that includes a representation of the reminder 26 (of FIG. 1) to consume at least one particular ingestible substance to communication unit 38. Communication unit 38 may send the data that includes the representation of the reminder to visual display device 172 using external network 156. Visual display device 172, in response to receiving the data using external network 156, may cause presence-sensitive display 174 to output the reminder. In response to a user performing a gesture at presence-sensitive display 174 (e.g., at a region of presence-sensitive display 174 that outputs the graphical keyboard), visual display device 172 may send an indication of the gesture to computing device 4 using external network 156. Communication unit 38 of may receive the indication of the gesture, and send the indication to computing device 4.

In response to receiving an indication of at least one gesture detected at a presence-sensitive input device, computing device 4 may handle the reminder. For example, computing device 4 may send data that includes an indication to stop displaying the representation of the reminder to visual display device 172 using external network 156. In some instances, computing device 4 may send a second instance of data that includes the representation of the reminder to visual display device 172 using external network 156 in an amount of time after the first instance. In some examples, this amount of time may be 5 minutes, 15 minutes, 30 minutes, an amount of time specified by the user, an amount of time specified by the application developer, or some other amount of time.

In some examples, a user may manually input data into computing device 4 to indicate that the user is currently eating. In another example, computing device 4 may refer to a time schedule at which a user is supposed to take a medication. For instance, a user may only need to take a medication in the morning, only at night, twice a day, or once every two hours, among other things. Computing device 4 may only attempt to determine whether a user is currently consuming an ingestible substance if the current time is close to a time on the time schedule.

As described in this disclosure, rather than outputting a medication reminder based solely on time or a location, a computing device may determine whether the user is eating based on activities that are more correlative with eating than time and/or location and issue a reminder to consume at least one particular ingestible substance, such as a medication, based on those correlative activities that may be different than a time and/or a location. For instance, if a time-based reminder is issued before a user has eaten, then a user may forget by the time they actually consume food. Further, if a time-based reminder is issued too far after a user has eaten, the benefits of having food in a user's stomach when the medication is consumed may have passed. Other medication reminders may assume that a user is eating based on a current location, but make no determination if the user actually is eating, causing improper reminders to be issued to a user. By making a determination of whether the user is currently consuming an ingestible substance, rather than making an inference of eating based solely on a time or a current location, techniques of this disclosure allow for a more precise reminder schedule that a user is more likely follow when the schedule includes medication that must be taken at around the same time that a user is eating.

Example 1

A method comprising generating, by one or more sensors of a computing device and at approximately a time that a user is eating, at least one computer-generated indication; determining, by the computing device and based at least in part on the at least one computer-generated indication and pre-defined activity data that are indicative of an act of a human consuming an ingestible substance, whether the user is currently consuming an ingestible substance; and responsive to determining that the user is currently consuming the ingestible substance, outputting, by the computing device, a reminder to consume at least one particular ingestible substance.

Example 2

The method of example 1, wherein determining whether the user is currently consuming the ingestible substance comprises determining, by the computing device and based at least in part on the pre-defined activity data and the at least one computer-generated indication, a degree of confidence that indicates a confidence that the user is currently consuming the ingestible substance; comparing, by the computing device, the degree of confidence to a threshold to determine whether the degree of confidence satisfies the threshold; and responsive to determining that the degree of confidence satisfies the threshold, determining, by the computing device, that the user is currently consuming the ingestible substance.

Example 3

The method of example 1, wherein the computer-generated indication is a first computer-generated indication and the pre-defined activity data is first pre-defined activity data, wherein determining whether the user is currently consuming the ingestible substance comprises: determining, by the computing device, a first difference between the first computer-generated indication and the first pre-defined activity data; determining, by the computing device, a second difference between a second computer-generated indication and second pre-defined activity data; applying, by the computing device, a first weight, corresponding to the first computer-generated indication, to the first difference to generate a first weighted difference value; applying, by the computing device, a second weight, corresponding to the second computer-generated indication, to the second difference to generate a second weighted difference value; aggregating, by the computing device, the first and second weighted difference values to generate an aggregated weighted difference value; and determining, by the computing device and based at least in part on the aggregated weighted difference value, whether the user is currently consuming the ingestible substance.

Example 4

The method of any of examples 1-3, wherein the at least one computer-generated indication comprises at least one of a picture of food, a picture of utensils, motion data obtained from the one or more sensors, a blood sugar level, a time, a sound, a picture of a cheekbone, and GPS coordinates.

Example 5

The method of any of examples 1-4, wherein the pre-defined activity data comprises at least one of image data of portions of food, a motion profile, image data of portions of a cheekbone, image data of portions of utensils, a mapping service to look up a restaurant, an eating schedule, an eating time, ambient audio to determine co-presence of others who are eating, a blood sugar level, motion data, a database of coordinates of restaurants, and a trained classifier.

Example 6

The method of any of examples 1-5, wherein the at least one particular ingestible substance is at least one medication.

Example 7

The method of any of examples 1-6, further comprising: receiving, by the computing device, data from the one or more sensors that are operably coupled to the computing device, wherein the computing device generates the computer-generated indication based on the data received from the one or more sensors.

Example 8

The method of example 7, wherein the one or more sensors comprise at least one of an accelerometer, a gyrometer, a blood sugar measuring sensor, a camera, an audio input device, a global positioning system, and a clock.

Example 9

The method of any of examples 1-8, further comprising responsive to determining that the user is consuming the ingestible substance, generating, by the computing device, at least one difference between the at least one computer-generated indication and the pre-defined activity data; and updating, by the computing device, the pre-defined activity data based on the at least one difference, wherein determining whether the user is currently consuming the ingestible substance comprises determining, by the computing device and based at least in part on the at least one computer-generated indication and the updated pre-defined activity data, whether the user is currently consuming the ingestible substance.

Example 10

The method of any of examples 1-9, wherein a time duration comprises a range of time, wherein the determining the at least one computer-generated indication at the time that the user is eating is within the time duration.

Example 11

The method of any of examples 1-10, wherein the reminder comprises at least one of a text message, an email, a vibration on a watch, a user interface element for display on the computing device, a flashing light mounted on computing device, or an audio message.

Example 12

A computing device comprising: at least one processor; and at least one module, operable by the at least one processor to: generate, at approximately a time that a user is eating, at least one computer-generated indication; determine, based at least in part on the at least one computer-generated indication and pre-defined activity data that are indicative of an act of a human consuming an ingestible substance, whether the user is currently consuming an ingestible substance; and responsive to determining that the user is currently consuming the ingestible substance, output a reminder to consume at least one particular ingestible substance.

Example 13

The computing device of example 12, wherein the at least one module is further operable by the at least one processor to: determine, based at least in part on the pre-defined activity data and the at least one computer-generated indication, a degree of confidence that indicates a confidence that the user is currently consuming the ingestible substance; compare the degree of confidence to a threshold to determine whether the degree of confidence satisfies the threshold; and responsive to determining that the degree of confidence satisfies the threshold, determine that the user is currently consuming the ingestible substance.

Example 14

The computing device of example 12, wherein the computer-generated indication is a first computer-generated indication and the pre-defined activity data is first pre-defined activity data, and wherein the at least one module is operable by the at least one processor to: determine a first difference between the first computer-generated indication and the first pre-defined activity data; determine a second difference between a second computer-generated indication and second pre-defined activity data; apply a first weight, corresponding to the first computer-generated indication, to the first difference to generate a first weighted difference value; apply a second weight, corresponding to the second computer-generated indication, to the second difference to generate a second weighted difference value; aggregate the first and second weighted difference values to generate an aggregated weighted difference value; and determine, based at least in part on the aggregated weighted difference value, whether the user is currently consuming the ingestible substance.

Example 15

The computing device of any of examples 12-14, wherein the at least one module is operable by the at least one processor to: responsive to determining that the user is consuming the ingestible substance, generate at least one difference between the at least one computer-generated indication and the pre-defined activity data; and update the pre-defined activity data based on the difference to generated updated pre-defined activity data, wherein the at least one module is operable by the at least one processor to determine, based at least in part on the at least one computer-generated indication and the updated pre-defined activity data, whether the user is currently consuming the ingestible substance.

Example 16

The computing device of any of examples 12-15, wherein the computing device is at least one of a computerized watch, computerized eyewear, computerized headwear, computerized gloves, a blood sugar monitoring device, a tablet computer, a mobile phone, a personal digital assistant (PDA), a laptop computer, a gaming system, a media player, an e-book reader, a television platform, an automobile navigation system, and a camera.

Example 17

A computer-readable storage medium encoded with instructions that, when executed, cause at least one processor of a computing device to: generate, at approximately a time that a user is eating, at least one computer-generated indication; determine, based at least in part on the at least one computer-generated indication and pre-defined activity data that are indicative of an act of a human consuming an ingestible substance, whether the user is currently consuming an ingestible substance; and responsive to determining that the user is currently consuming the ingestible substance, output a reminder to consume at least one medication.

Example 18

The computer readable storage medium of example 17, wherein the instructions causing the at least one processor to determine whether the user is currently consuming the ingestible substance further comprise instructions that, when executed, cause the at least one processor to: determine, based at least in part on the pre-defined activity data and the at least one computer-generated indication, a degree of confidence that indicates a confidence that the user is currently consuming the ingestible substance; compare the degree of confidence to a threshold to determine whether the degree of confidence satisfies the threshold; and responsive to determining that the degree of confidence satisfies the threshold, determine that the user is currently consuming the ingestible substance.

Example 19

The computer readable storage medium of claim 17, wherein the computer-generated indication is a first computer-generated indication and the pre-defined activity data is first pre-defined activity data, and wherein the instructions causing the at least one processor to determine whether the user is currently consuming the ingestible substance comprise instructions that, when executed, cause the at least one processor to: determine a first difference between the first computer-generated indication and the first pre-defined activity data; determine a second difference between a second computer-generated indication and second pre-defined activity data; apply a first weight, corresponding to the first computer-generated indication, to the first difference to generate a first weighted difference value; apply a second weight, corresponding to the second computer-generated indication, to the second difference to generate a second weighted difference value; aggregate the first and second weighted difference values to generate an aggregated weighted difference value; and determine, based at least in part on the aggregated weighted difference value, whether the user is currently consuming the ingestible substance.

Example 20

The computer-readable storage medium of any of examples 17-19, wherein the instructions, when executed, further cause the at least one processor to: responsive to determining that the user is consuming the ingestible substance, generate at least one difference between the at least one computer-generated indication and the pre-defined activity data; and update the pre-defined activity data based on the difference to generated updated pre-defined activity data, wherein the computer-readable storage medium is further encoded with instructions that, when executed, cause the one or more processors to determine, based at least in part on the at least one computer-generated indication and the updated pre-defined activity data, whether the user is currently consuming the ingestible substance.

Example 21

A computing device comprising means for generating, at approximately a time that a user is eating, at least one computer-generated indication; means for determining, based at least in part on the at least one computer-generated indication and pre-defined activity data that are indicative of an act of a human consuming an ingestible substance, whether the user is currently consuming an ingestible substance; and means for outputting, by the computing device, a reminder to consume at least one particular ingestible substance responsive to determining that the user is currently consuming the ingestible substance.

Example 22

A computing device comprising means for performing the method of any of examples 1-11.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used may refer to any of the foregoing structure or any other structure suitable for implementation of the techniques described. In addition, in some aspects, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

It is to be recognized that depending on the embodiment, certain acts or events of any of the methods described herein can be performed in a different sequence, may be added, merged, or left out altogether (e.g., not all described acts or events are necessary for the practice of the method). Moreover, in certain embodiments, acts or events may be performed concurrently, e.g., through multi-threaded processing, interrupt processing, or multiple processors, rather than sequentially.

In some examples, a computer-readable storage medium may include a non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described. These and other examples are within the scope of the following claims.

The invention claimed is:

1. A computing device for reminding a user to consume at least one particular ingestible substance based on a determination that the user is currently eating, the computing device comprising:
   at least one processor; and
   at least one module, operable by the at least one processor to:
   generate, based on motion data received from one or more sensors operably coupled to the computing device, and at a time that the user is eating, at least one indication of user activity indicating one or more motions of an arm of the user, wherein the one or more sensors are located on the arm of the user;
   determine, based on pre-defined motion data that is indicative of an act of a human consuming an ingestible substance and the at least one indication of user activity, a degree of confidence that indicates a confidence that the user is currently consuming the ingestible substance;
   compare the degree of confidence to a threshold to determine whether the degree of confidence satisfies the threshold;
   responsive to determining that the degree of confidence satisfies the threshold, determine that the user is currently consuming the ingestible substance; and
   responsive to determining that the user is currently consuming the ingestible substance, output a reminder to consume the at least one particular ingestible substance.

2. The computing device of claim 1, wherein the at least one indication of user activity comprises a first indication of user activity, wherein the one or more sensors comprise a first set of one or more sensors, and wherein the at least one module is operable by the at least one processor to:
   determine a first difference between the first indication of user activity and the pre-defined motion data;
   generate, by a second set of one or more sensors operably coupled to the computing device, based on data received from the second set of one or more sensors, a second indication of user activity, wherein the second set of one or more sensors are different from the first set of one or more sensors;
   determine a second difference between the second indication of user activity and pre-defined activity data;
   apply a first weight, corresponding to the first indication of user activity, to the first difference to generate a first weighted difference value;
   apply a second weight, corresponding to the second indication of user activity, to the second difference to generate a second weighted difference value;
   aggregate the first and second weighted difference values to generate an aggregated weighted difference value; and
   determine, based on the aggregated weighted difference value, whether the user is currently consuming the ingestible substance.

3. The computing device of claim 1, wherein the at least one module is operable by the at least one processor to:
   responsive to determining that the user is consuming the ingestible substance, generate at least one difference between the at least one indication of user activity and the pre-defined motion data; and
   update the pre-defined motion data based on the difference to generated updated pre-defined motion data,
   wherein the at least one module is operable by the at least one processor to determine, based on the at least one indication of user activity and the updated pre-defined motion data, whether the user is currently consuming the ingestible substance.

4. The computing device of claim 1, wherein the computing device comprises a wearable computing device configured to be worn on the arm of the user.

5. The computing device of claim 1, wherein the one or more sensors are physically attached to the computing device.

6. A method for reminding a user to consume at least one particular ingestible substance based on a determination that the user is currently eating, the method comprising:
   generating, by one or more sensors of a computing device, based on motion data received from the one or more sensors, and at a time that a user is eating, at least one indication of user activity indicating one or more motions of an arm of the user, wherein the one or more sensors are located on the arm of the user;

determining, by the computing device and based on pre-defined motion data that is indicative of an act of a human consuming an ingestible substance and the at least one indication of user activity, a degree of confidence that indicates a confidence that the user is currently consuming the ingestible substance;

comparing, by the computing device, the degree of confidence to a threshold to determine whether the degree of confidence satisfies the threshold;

responsive to determining that the degree of confidence satisfies the threshold, determining, by the computing device that the user is currently consuming the ingestible substance; and responsive to determining that the user is currently consuming the ingestible substance, outputting, by the computing device, a reminder to consume the at least one particular ingestible substance.

7. The method of claim 6, wherein the at least one indication of user activity comprises a first indication of user activity, wherein the one or more sensors comprise a first set of one or more sensors, wherein determining whether the user is currently consuming the ingestible substance comprises:

determining, by the computing device, a first difference between the first indication of user activity and the pre-defined motion data;

generating, by a second set of one or more sensors operably coupled to the computing device, based on data received from the second set of one or more sensors, a second indication of user activity, wherein the second set of one or more sensors are different from the first set of one or more sensors;

determining, by the computing device, a second difference between the second indication of user activity and pre-defined activity data;

applying, by the computing device, a first weight, corresponding to the first indication of user activity, to the first difference to generate a first weighted difference value;

applying, by the computing device, a second weight, corresponding to the second indication of user activity, to the second difference to generate a second weighted difference value;

aggregating, by the computing device, the first and second weighted difference values to generate an aggregated weighted difference value; and determining, by the computing device and based on the aggregated weighted difference value, whether the user is currently consuming the ingestible substance.

8. The method of claim 7, wherein the pre-defined activity data comprises at least one of image data of portions of food, a motion profile, image data of portions of a cheekbone, image data of portions of utensils, a mapping service to look up a restaurant, an eating schedule, an eating time, ambient audio to determine co-presence of others who are eating, a blood sugar level, motion data, a database of coordinates of restaurants, and a trained classifier.

9. The method of claim 6, wherein the at least one particular ingestible substance is at least one medication.

10. The method of claim 6, wherein the one or more sensors comprise at least one of an accelerometer and a gyrometer.

11. The method of claim 6, further comprising:

responsive to determining that the user is consuming the ingestible substance, generating, by the computing device, at least one difference between the at least one indication of user activity and the pre-defined motion data; and updating, by the computing device, the pre-defined motion data based on the at least one difference, wherein determining whether the user is currently consuming the ingestible substance comprises determining, by the computing device and based on the at least one indication of user activity and the updated pre-defined motion data, whether the user is currently consuming the ingestible substance.

12. The method of claim 6, wherein generating the at least one indication of user activity at the time that the user is eating comprises generating the at least one indication of user activity within a time duration, wherein the time duration comprises a range of time.

13. The method of claim 6, wherein the reminder comprises at least one of a text message, an email, a vibration on a watch, a user interface element for display on the computing device, a flashing light mounted on computing device, or an audio message.

14. The method of claim 6, wherein the received motion data comprises at least one of a speed of the one or more motions of the arm of the user or a set of one or more positions of the arm during the one or more motions of the arm of the user, wherein the received motion data is measured by one of an accelerometer or a gyrometer and converted into one or more motion vectors.

15. A non-transitory computer-readable storage medium encoded with instructions that, when executed, cause at least one processor of a computing device to:

generate, at a time that a user is eating and based on motion data received from one or more sensors operably coupled to the computing device and located on an arm of the user, at least one indication of user activity indicating one or more motions of the arm of the user;

determine, based on pre-defined motion data that is indicative of an act of a human consuming an ingestible substance and the at least one indication of user activity, a degree of confidence that indicates a confidence that the user is currently consuming the ingestible substance;

compare the degree of confidence to a threshold to determine whether the degree of confidence satisfies the threshold;

responsive to determining that the degree of confidence satisfies the threshold, determine that the user is currently consuming the ingestible substance; and responsive to determining that the user is currently consuming the ingestible substance, output a reminder to consume the at least one particular ingestible substance.

16. The non-transitory computer readable storage medium of claim 15, wherein the at least one indication of user activity comprises a first indication of user activity, wherein the one or more sensors comprise a first set of one or more sensors, and wherein the instructions causing the at least one processor to determine whether the user is currently consuming the ingestible substance comprise instructions that, when executed, cause the at least one processor to:

determine a first difference between the first indication of user activity and the pre-defined motion data;

generate, by a second set of one or more sensors operably coupled to the computing device, based on data received from the second set of one or more sensors, a second indication of user activity, wherein the second set of one or more sensors are different from the first set of one or more sensors;

determine a second difference between the second indication of user activity and pre-defined activity data;

apply a first weight, corresponding to the first indication of user activity, to the first difference to generate a first weighted difference value;

apply a second weight, corresponding to the second indication of user activity, to the second difference to generate a second weighted difference value;

aggregate the first and second weighted difference values to generate an aggregated weighted difference value; and determine, based on the aggregated weighted difference value, whether the user is currently consuming the ingestible substance.

17. The non-transitory computer-readable storage medium of claim 15, wherein the instructions, when executed, further cause the at least one processor to:

responsive to determining that the user is consuming the ingestible substance, generate at least one difference between the at least one indication of user activity and the pre-defined motion data; and update the pre-defined motion data based on the difference to generated updated pre-defined motion data, wherein the computer-readable storage medium further comprises instructions that, when executed, cause the one or more processors to determine, based on the at least one indication of user activity and the updated pre-defined motion data, whether the user is currently consuming the ingestible substance.

* * * * *